United States Patent [19]

Kitaura et al.

[11] Patent Number: 4,698,349
[45] Date of Patent: Oct. 6, 1987

[54] QUINOLIZINONE COMPOUNDS, AND PHARMACEUTICAL COMPOSITION COMPRISING THE SAME, USEFUL AS ANTI-ULCERATIVE AND ANTI-ALLERGIC AGENTS

[75] Inventors: Yoshihiko Kitaura, Nagoya; Teruo Oku, Osaka; Hideo Hirai, Nishinomiya; Tosiyuki Yamamoto, Ikeda; Masashi Hashimoto, Nakayama, all of Japan

[73] Assignee: Fujisawa Pharmaceutical Co., Ltd., Osaka, Japan

[21] Appl. No.: 770,953

[22] Filed: Aug. 30, 1985

Related U.S. Application Data

[63] Continuation-in-part of Ser. No. 712,435, Mar. 18, 1985, Pat. No. 4,650,804.

[30] Foreign Application Priority Data

Mar. 30, 1984 [GB]  United Kingdom ................ 8408292
Nov. 23, 1984 [GB]  United Kingdom ................ 8429710

[51] Int. Cl.⁴ .................. A61K 31/345; C07D 455/02
[52] U.S. Cl. ..................................... 514/306; 546/138
[58] Field of Search ......................... 546/138; 514/306

[56] References Cited

PUBLICATIONS

Kappe, T. Chem Abstracts, vol. 67;82039q (1967).
Acheson et al., Chem Abstracts, vol. 62;16188h (1965).
Kappe et al, Chem Abstracts, vol. 99;88023n (1983).
Ibid, vol. 78;111166p (1973).
Thyagarajan et al., Chem Abstracts vol. 63;4255e (1965).
Allen et al., Chem Abstracts, vol. 54;1533e (1960).
Leaver et al. Chem Abstracts vol. 60; 54549 (1964).
Kobayashi et al, Chem Abstracts, vol. 88;44882k (1978).
Goodman et al., The Pharmacological Basis of Therapeutics 6 ed. p. 28.

Primary Examiner—Henry R. Jiles
Assistant Examiner—J. Richter
Attorney, Agent, or Firm—Oblon, Fisher, Spivak, McClelland, & Maier

[57] ABSTRACT

The invention relates to novel quinolizinone compounds, of inhibitory activity on allergies and ulcers, of the formula:

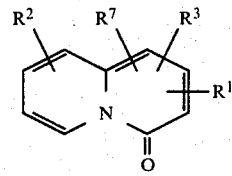

wherein
$R^1$ is carboxy, carbamoyl $Y^1$, phenylcarbamoyl which may have hydroxy, cyano or thiocarbamoyl,
$R^7$ is hydrogen or aryl selected from phenyl, tolyl, xylyl, cumenyl, naphthyl and biphenylyl;
$R^2$ is hydrogen, hydroxy, lower alkyl or lower alkoxy; and
$R^3$ is hydrogen, hydroxy, lower alkyl, lower alkoxy, lower alkenyloxy, phenyl, naphthyl, biphenylyl, phenyl having one or more substituent(s) selected from halogen, lower alkyl and lower alkoxy, arylthio selected from phenylthio, tolylthio, xylylthio, cumenylthio, naphthylthio and biphenylylthio, aroyl selected from benzoyl, toluoyl and naphthoyl, ar(lower)alkyl selected from phenyl(lower)alkyl, tolyl(lower)alkyl, xylyl(lower)alkyl, cumenyl(lower)alkyl, naphthyl(lower)alkyl and biphenylyl(lower)alkyl, arenesulfonyl selected from benzenesulfonyl and p-toluenesulfonyl, arylamino selected from phenylamino, naphthylamino, biphenylylamino, phenylamino having lower alkyl on the nitrogen atom or aryloxy selected from phenoxy and tolyloxy; or pharmaceutically acceptable salts thereof.

13 Claims, No Drawings

QUINOLIZINONE COMPOUNDS, AND PHARMACEUTICAL COMPOSITION COMPRISING THE SAME, USEFUL AS ANTI-ULCERATIVE AND ANTI-ALLERGIC AGENTS

This application is a continuation-in-part of U.S. application Ser. No. 712,435 filed Mar. 18, 1985 and now U.S. Pat. No. 4,650,804.

This invention relates to quinolizinone compound and a salt thereof. More particularly, it relates to a new quinolizinone compound and a pharmaceutically acceptable salt thereof which have inhibitory activities on allergy and ulcer, to processes for preparation thereof, and to a pharmaceutical composition comprising the same.

Accordingly, one object of this invention is to provide the new and useful quinolizinone compound and a pharmaceutically acceptable salt thereof.

Another object of this invention is to provide processes for preparation of said quinolizinone compound and the salt thereof.

A further object of this invention is to provide a pharmaceutical composition comprising, as an active ingredient, said quinolizinone compound or the pharmaceutically acceptable salt thereof.

Still further object of this invention is to provide a therapeutical method for treatment of allergic disease and ulcer in human being and animals.

The quinolizinone compound of this invention can be represented by the following formula (I):

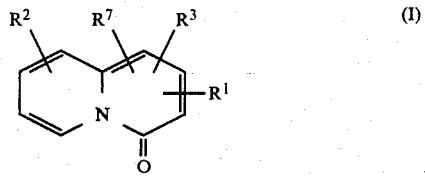

wherein
$R^1$ is carboxy, amidated carboxy, cyano, thiocarbamoyl or tetrazolyl group;
$R^7$ is hydrogen or aryl;
$R^2$ is hydrogen, hydroxy, lower alkyl or lower alkoxy;
$R^3$ is hydrogen, hydroxy, lower alkyl, lower alkoxy, carboxy, protected carboxy, lower alkenyloxy, aryl which may have suitable substituent(s), arylthio, aroyl, ar(lower)alkyl, arenesulfonyl, arylamino which may have a suitable substituent or aryloxy; and
$R^2$ and $R^3$ can be located at any place on the quinolizinone ring and can be linked together to form —CH$_2$CH$_2$CH$_2$—, —CH=CH— or —CH=CH—CH=CH—.

According to this invention, the object compound (I) can be prepared by the processes as illustrated by the following schemes.

Process 1:

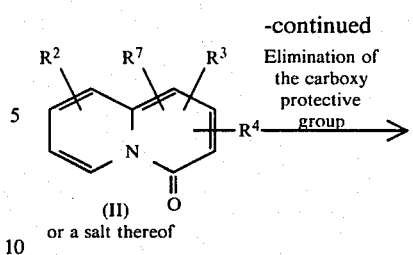
(II)
or a salt thereof

Elimination of the carboxy protective group →

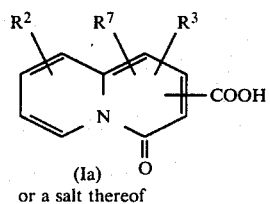
(Ia)
or a salt thereof

Process 2:

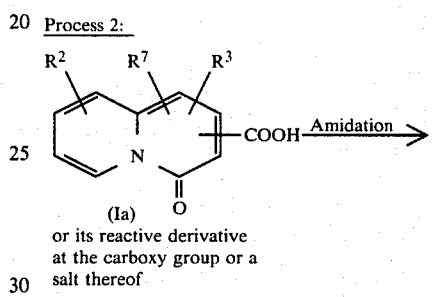
(Ia)
or its reactive derivative at the carboxy group or a salt thereof Amidation →

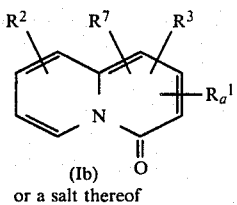
(Ib)
or a salt thereof

Process 3:

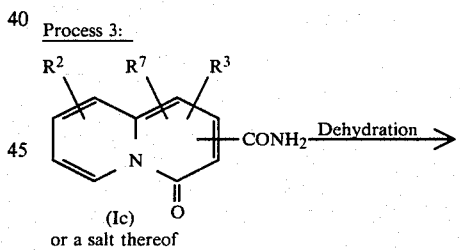
(Ic)
or a salt thereof

Dehydration →

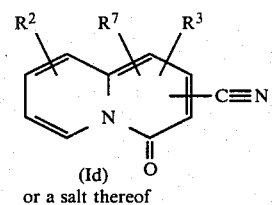
(Id)
or a salt thereof

Process 4:

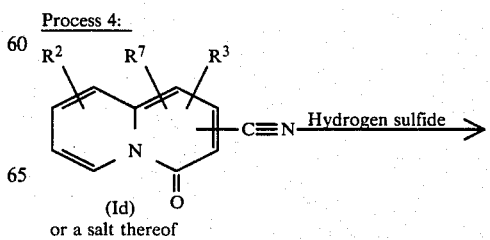
(Id)
or a salt thereof

Hydrogen sulfide →

-continued

Process 5:

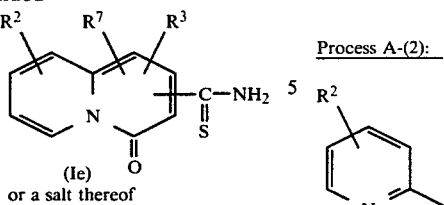
(Ie) or a salt thereof

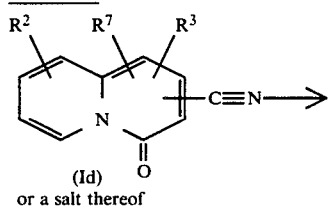
(Id) or a salt thereof

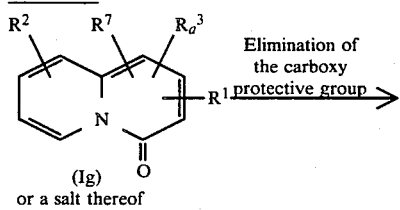
(If) or a salt thereof

Process 6:

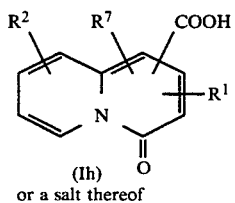
(Ig) or a salt thereof

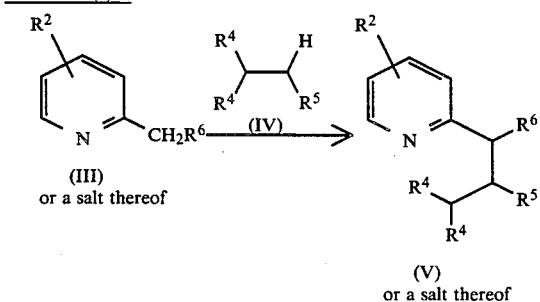
(Ih) or a salt thereof wherein
R$^2$, R$^3$ and R$^7$ are each as defined above,
R$_a^1$ is amidated carboxy, and
R$^4$ and R$_a^3$ are each protected carboxy.

Among the starting compounds in the present invention, the compound (II) can be prepared by the processes which are illustrated in the following schemes.

Process A-(1):

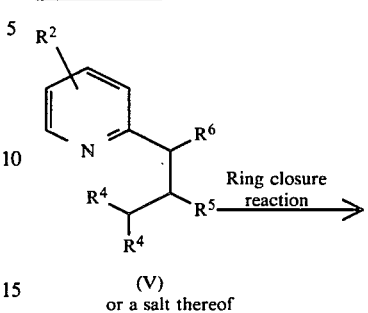
(III) or a salt thereof → (V) or a salt thereof

Process A-(2):

(V) or a salt thereof —Ring closure reaction→

(IIa) or a salt thereof

Process B-(1):

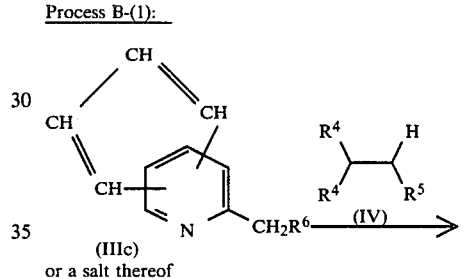
(IIIc) or a salt thereof (Vc) or a salt thereof

Process B-(2):

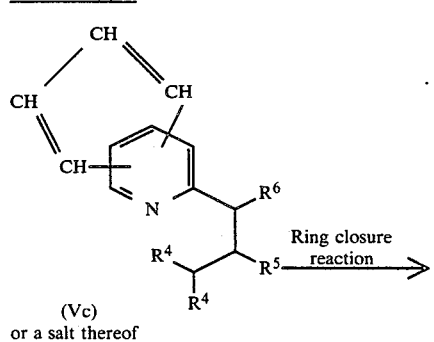
(Vc) or a salt thereof —Ring closure reaction→

-continued

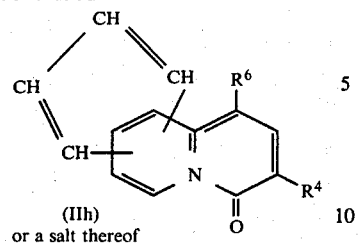
(IIh)
or a salt thereof

Process C-(1):

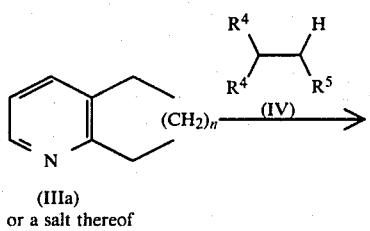  (IV) ⟶

(IIIa)
or a salt thereof

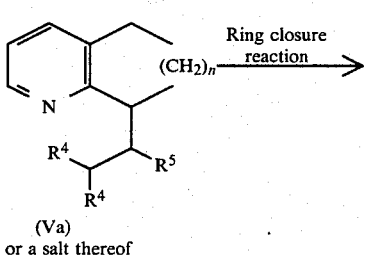
(Va)
or a salt thereof

Process C-(2):

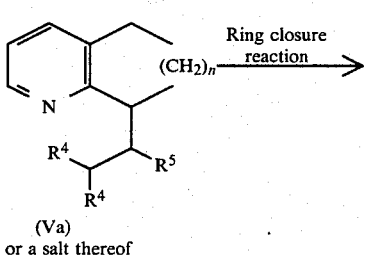 Ring closure reaction ⟶

(Va)
or a salt thereof

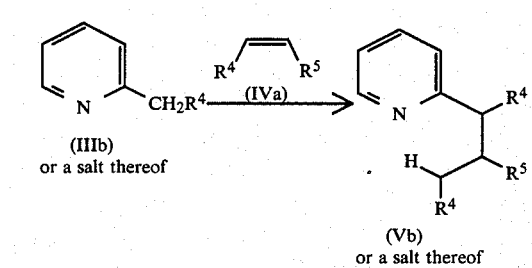
(IIb)
or a salt thereof

Process D-(1):

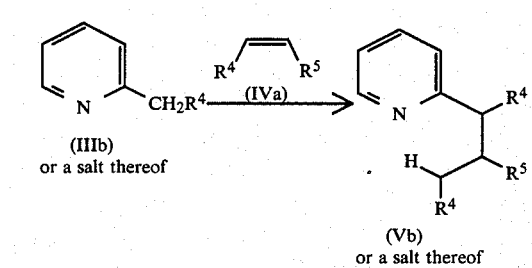 (IVa) ⟶

(IIIb)
or a salt thereof (Vb)
or a salt thereof

Process D-(2):

-continued

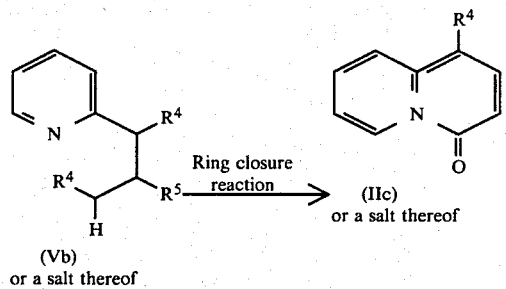 Ring closure reaction ⟶ (IIc) or a salt thereof (Vb)
or a salt thereof Process E:

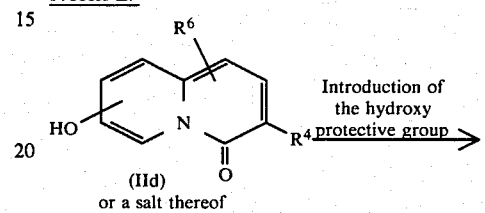 Introduction of the hydroxy protective group ⟶

(IId)
or a salt thereof

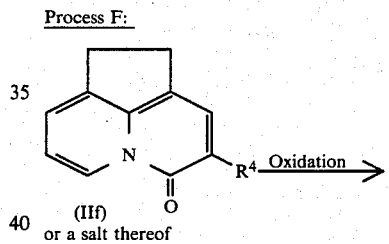
(IIe)
or a salt thereof

Process F:

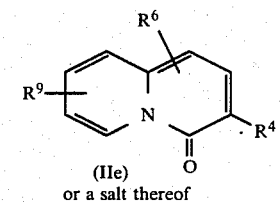 Oxidation ⟶

(IIf)
or a salt thereof

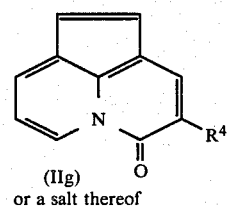
(IIg)
or a salt thereof

Process G:

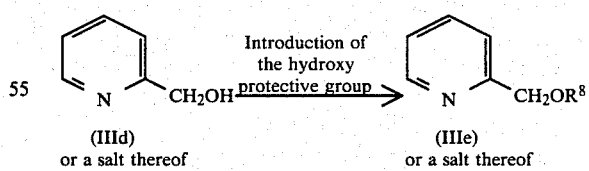

(IIId)
or a salt thereof (IIIe)
or a salt thereof

Process H:

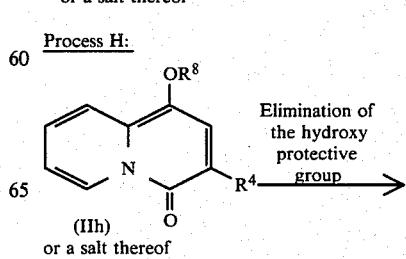 Elimination of the hydroxy protective group ⟶

(IIh)
or a salt thereof

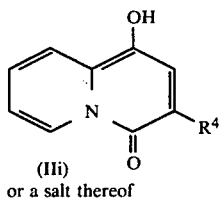

(IIi)
or a salt thereof

Process I:

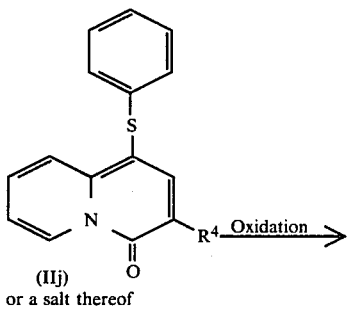

(IIj)
or a salt thereof

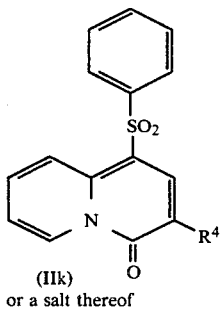

(IIk)
or a salt thereof wherein $R^2$, $R^4$ and $R^7$ are each as defined above, $R^5$ is lower alkoxy, $R^6$ is hydrogen, protected hydroxy, lower alkyl, lower alkoxy, carboxy, protected carboxy, lower alkenyloxy, aryl which may have suitable substituent(s), arylthio, aroyl, ar(lower)alkyl, arenesulfonyl, arylamino which may have a suitable substituent or aryloxy, $R^8$ is hydroxy protective group, $R^9$ is protected hydroxy and n is 1 or 2.

Suitable pharmaceutically acceptable salts of the object compounds (I) are conventional non-toxic salt and include an acid addition salt such as an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydriodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention include within the scope thereof are explained in detail as follows.

The term "lower" is intended to mean 1 to 6 carbon atoms, unless otherwise indicated.

Suitable "lower alkyl" and "lower alkyl" moiety in "ar(lower)alkyl" may include straight or branched one, having 1 to 6 carbon atom(s), such as methyl, ethyl, propyl, isopropyl, butyl, t-butyl, pentyl, hexyl or the like.

Suitable "lower alkoxy" may include methoxy, ethoxy, propoxy, isopropoxy, butoxy, isobutoxy, tert-butoxy, pentyloxy, tert-pentyloxy, hexyloxy, and the like, preferably one having 1 to 4 carbon atom(s).

Suitable "lower alkenyloxy" may include vinyloxy, 1-propenyloxy, allyloxy, 1-butenyloxy, 2-butenyloxy, 2-pentenyloxy, and the like, preferably ones having 2 to 4 carbon atoms.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.]lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.).

Suitable "amidated carboxy" may include amide (—CONH$_2$) which may have suitable substituent(s) on the nitrogen atom, wherein said substituent(s) may include heterocyclic group which may have suitable substituent(s), aryl which may have suitable substituent(s) as mentioned below, and the like.

"Heterocyclic group" as mentioned above means, in detail, saturated or unsaturated, monocyclic or polycyclic heterocyclic group containing at least one heteroatom such as an oxygen, sulfur, nitrogen atom and the like.

And, especially preferably heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), triazinyl (e.g. 1,2,3-triazinyl, 1,2,4-triazinyl, 1,3,5-triazinyl, etc.), etc.; saturated 3 to 8-membered (more preferably 5 or 6-membered)heteromonocyclic group containing 1 to 4 nitrogen atom(s), for example, pyrrolidinyl, imidazolidinyl, piperidino, piperazinyl, etc.; unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.; unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.; saturated 3 to 8-membered (more preferably 5 or 6-membered) heteromonocyclic group containing 1 to 2 oxygen atom(s) and 1 to 3 nitrogen atom(s), for example, morpholinyl, syndonyl, etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered (more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.; saturated 3 to 8-membered (more preferably 5 or 6-membered) heteromonocyclic group containing 1 to 2 sulfur atom(s) and 1 to 3 nitrogen atom(s), for example, thiazolidinyl, etc.; unsaturated 3 to 8-membered (more preferably 5 or 6-membered) heteromonocyclic group containing 1 to 2 sulfur atom(s), for example, thienyl, dihydrodithiinyl, dihydrodithionyl, etc.; unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered (more preferably 5 to 6-membered) heteromonocyclic group containing an oxygen atom, for example, furyl, etc.; unsaturated 3 to 8-membered (more preferably 5 or 6-membered) heteromonocyclic group containing an oxygen atom and 1 to 2 sulfur atom(s), for example, dihydrooxathiinyl, etc.; unsaturated condensed heterocyclic group containing 1 to 2 sulfur atom(s), for example, benzothienyl, benzodithiinyl, etc.; unsaturated condensed heterocyclic group containing an oxygen atom and 1 to 2 sulfur atom(s), for example, benzoxathiinyl, etc. and the like, wherein said "heterocyclic group" may have one or more suitable substituent(s) such as halogen (e.g., chlorine, bromine, iodine or fluorine), lower alkyl (e.g., methyl, ethyl, propyl, etc.) as stated above, amino, or the like.

Suitable "protected hydroxy" may include a hydroxy group protected by a conventional hydroxyprotective group, for example, lower alkyl (e.g. methyl, ethyl, propyl, n-butyl, etc.), lower alkenyl (e.g. vinyl, allyl, etc.), ar(lower)alkyl such as mono- or di- or triphenyl(lower)alkyl (e.g. benzyl, benzhydryl, trityl, etc.), etc., trisubstituted silyl such as tri(lower)alkylsilyl (e.g. trimethylsilyl, triethylsilyl, isopropyldimethylsilyl, tert-butyldimethylsilyl, diisopropylmethylsilyl, etc.), triarylsilyl (e.g. triphenylsilyl, etc.), triar(lower)alkylsilyl (e.g. tribenzylsilyl, etc.), etc., and the like.

Suitable "aryl" may include phenyl, tolyl, xylyl, cumenyl, naphthyl, biphenylyl, and the like, which may have one or more suitable substituent(s) such as amino, nitro, halogen (e.g. fluorine, chlorine, bromine, iodine, etc.), lower alkoxy as exemplified above, carboxy, a protected carboxy group as exemplified above, hydroxy, and the like.

Suitable "aryl" moiety in the terms "arylthio", "ar(lower)alkyl" and "arylamino" can be referred to the ones as exemplified above.

Suitable "aroyl" may include benzoyl, toluoyl, naphthoyl, and the like.

Suitable "arenesulfonyl" may include benzenesulfonyl, p-toluenesulfonyl, and the like.

The aforesaid "arylamino" may have a suitable substituent such as lower alkyl (e.g. methyl, ethyl, etc.) on the nitrogen atom, and the like.

Suitable "aryloxy" may include phenoxy, tolyloxy, and the like.

Suitable "hydroxy protective group" can be referred to the ones as exemplified above.

Preferable "amidated carboxy" may be carbamoyl, pyridylamido, pyrimidinylamido which may have lower alkyl, pyrazinylamido, phenylamido which may have hydroxy, thiazolylamido, triazinylamido, triazolylamido which may have amino, pyridazinylamido which may have halogen, or tetrazolylamido, or the like.

The processes for preparing the object compounds (I) of the present invention are explained in detail in the following.

Process 1

The object compound (Ia) or a salt thereof can be prepared by subjecting the compound (II) or a salt thereof to elimination reaction of the carboxy protective group.

Suitable salt of the compound (II) can be referred to the acid addition salt exemplified for the compound (I) and suitable salt of the compound (Ia) can be referred to the ones as exemplified for the compound (I).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-one, 1,4-diazabicyclo[2,2,-2]octane, 1,5-diazabicyclo-[5,4,0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitable be selected in accordance with the kind of the carboxy protective group and the elimination method.

The elimination using Lewis acid is preferable to eliminate substituted or unsubstituted ar(lower)alkyl ester and carried out by reacting the compound (II) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof.

The reduction elimination can be applied preferably for elimination of the protective group such as halo(-lower)alkyl (e.g. 2-iodoethyl, 2,2,2-trichloroethyl, etc.) ester, ar(lower)alkyl (e.g. benzyl, etc.) ester or the like.

The reduction method applicable for the elimination reaction may include, for example, reduction by using a combination of a metal (e.g. zinc, zinc amalgam, etc.) or a salt of chromium compound (e.g. chromous chloride, chromous acetate, etc.) and an organic or an inorganic acid (e.g. acetic acid, propionic acid, hydrochloric acid, etc.); and conventional catalytic reduction in the presence of a conventional metallic catalyst (e.g. palladium carbon, Raney nickel, etc.).

The reaction temperature is not critical, and the reaction is usually carried out under cooling, at ambient temperature or under warming.

The present elimination reaction of the carboxy protective group includes, within its scope, the case that another protected carboxy are converted into free carboxy during the reaction or the post-treating step of the present process.

Process 2

The object compound (Ib) or a salt thereof can be prepared by subjecting the compound (Ia) or its reactive derivative at the carboxy group or a salt thereof to amidation reaction.

Suitable salt of the compound (Ib) can be referred to the salt exemplified for the compound (I).

The amidating agent to be used in the present amidation reaction may include amine which may have suitable substituent(s) such as heterocyclic group which may have suitable substituent(s) or aryl which may have suitable substituent(s) on the nitrogen atom.

Suitable reactive derivative at the carboxy group of the compound (Ia) may include an acid halide, an acid anhydride, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; or an acitvated ester (e.g. cyanomethyl ester, methoxymethyl ester, dimethyliminomethyl [$(CH_3)_2N^{30}=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like.

When the compound (Ia) is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, 1,1'-carbonyldiimidazole, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

The reaction in the presence of a condensing agent is usually carried out in an anhydrous, but not critical conditions.

The reaction may be carried out in the presence of an inorganic or an organic base such as an alkali metal hydroxide (e.g. sodium hydroxide, potassium hydroxide, etc.), an alkali metal carbonate (e.g. sodium carbonate, potassium carbonate, etc.), an alkali metal bicarbonate (e.g. sodium bicarbonate, potassium bicarbonate, etc.), tri(lower)alkylamine (e.g. trimethylamine, triethylamine etc.), pyridine or its derivative (e.g. picoline, lutidine, 4-dimethylaminopyridine, etc.), or the like. In case that the base or the condensing agent to be used is in liquid, it can be used also as a solvent.

The reaction temperature is not critical, and the reaction is usually carried out under heating or under warming, preferably under heating.

Process 3

The object compound (Id) or a salt thereof can be prepared by subjecting the compound (Ic) or a salt thereof to dehydration reaction.

The dehydrating agent to be used in this dehydration reaction may include phosphoryl chloride, thionyl chloride, phosphorus pentoxide, phosphorus pentachloride, phosphorus pentabromide and the like.

The present reaction is usually carried out in a solvent such as dioxane, chloroform, methylene chloride, 1,2-dichloroethane, tetrahydrofuran, pyridine, acetonitrile, dimethylformamide or any other solvent which does not adversely affect the reaction.

The reaction temperature is not critical and the reaction is usually carried out at ambient temperature, under warming or heating.

Process 4

The object compound (Ie) or a salt thereof can be prepared by reacting the compound (Id) or a salt thereof with hydrogen sulfide.

The present reaction is usually carried out in a solvent such as dioxane, chloroform, methylene chloride, 1,2-dichloroethane, tetrahydrofuran, pyridine, acetonitrile, dimethylformamide or any other solvent which does not adversely affect the reaction.

The reaction temperature is not critical and the reaction is usually carried out at ambient temperature, under warming or heating.

Process 5

The object compound (If) or a salt thereof can be prepared by subjecting the compound (Id) or a salt thereof to the formation reaction of a tetrazole group.

Suitable salt of the compound (If) and (Id) can be referred to the acid addition salt exemplified for the compound (I).

The agent to be used in the present reaction may include conventional ones such as combination of alkali metal azide (e.g., potassium azide, sodium azide etc.) and ammonium halide (e.g. ammonium chloride), or the like.

The present reaction is usually carried out in a solvent such as dioxane, chloroform, methylene chloride, 1,2-dichloroethane, tetrahydrofuran, pyridine, acetonitrile, dimethylformamide or any other solvent which does not adversely affect the reaction.

The reaction temperature is not critical and the reaction is usually carried out under warming or heating.

Process 6

The compound (Ih) or a salt thereof can be prepared by subjecting the compound (Ig) or a salt thereof to elimination reaction of the carboxy protective group.

Suitable salts of the compounds (Ig) and (Ih) can be referred to the salts exemplified for the compound (I).

The present reaction can be carried out in a similar manner to that of Process 1 as mentioned above, and therefore the reaction modes and conditions (e.g. reaction temperature, solvent, etc.) are referred to those of Process 1.

Process A - (1)

The compound (V) or a salt thereof can be prepared by reacting the compound (III) or a salt thereof with the compound (IV).

Suitable salts of the compounds (III) and (V) can be referred to the acid addition salts exemplified for the compound (I).

The present reaction can be preferably carried out in the presence of alkyl lithium (e.g., n-butyl lithium), lithium diisopropylamide, alkalimetal alkoxide (e.g., sodium methoxide, sodium ethoxide etc.) and the like.

The present reaction is usually carried out in a solvent such as acetone, dioxane, acetonitrile, dimethylformamide, benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling, at ambient temperature or under heating.

Process A - (2)

The compound (IIa) or a salt thereof can be prepared by subjecting the compound (V) or a salt thereof to ring closure reaction.

Suitable salt of the compound (V) can be referred to the acid addition salt exemplified for the compound (I).

The present reaction may preferably be carried out in the presence of a suitable agent such as the mixture of diphenyl and diphenylether, which is used as heating medium.

The reaction temperature is not critical and the reaction is usually carried out under heating.

Process B - (1)

The compound (Vc) or a salt thereof can be prepared by reacting the compound (IIIc) or a salt thereof with the compound (IV).

Suitable salts of the compounds (Vc) and (IIIc) can be referred to the acid addition salts exemplified for the compound (I).

The present reaction can be carried out in a similar manner to that of Process A - (1) as mentioned above.

Process B - (2)

The compound (IIh) or a salt thereof can be prepared by subjecting the compound (Vc) or a salt thereof to ring closure reaction.

Suitable salts of the compound (IIh) and (Vc) can be referred to the acid addition salts exemplified for the compound (I).

The present reaction can be carried out in a similar manner to that of Process A - (2) as mentioned above.

Process C - (1)

The compound (Va) or a salt thereof can be prepared by reacting the compound (IIIa) or a salt thereof with the compound (IV).

Suitable salts of the compound (IIIa) and (Va) can be referred to the acid addition salts exemplified for the compound (I).

The present reaction can be carried out in a similar manner to that of Process A - (1) as mentioned above.

Process C - (2)

The compound (IIb) or a salt thereof can be prepared by subjecting the compound (Va) or a salt thereof to ring closure reaction.

Suitable salts of the compound (IIb) and (Va) can be referred to the acid addition salts exemplifed for the compound (I).

The present reaction can be carried out in a similar manner to that of Process A - (2) as mentioned above.

Process D - (1)

The compound (Vb) or a salt thereof can be prepared by reacting the compound (IIIb) or a salt thereof with the compound (IVa).

Suitable salts of the compounds (IIIb) and (Vb) can be referred to the acid addition salts exemplified for the compound (I).

The present reaction can be carried out in a similar manner to that of Process A - (1) as mentioned above.

Process D - (2)

The compound (IIc) or a salt thereof can be prepared by subjecting the compound (Vb) or a salt thereof to ring closure reaction.

Suitable salts of the compounds (IIc) and (Vb) can be referred to the acid addition salts exemplified for the compound (I).

The present reaction can be carried out in a similar manner to that of Process A - (2) as mentioned above.

Process E

The object compound (IIe) or a salt thereof can be prepared by subjecting the compound (IId) or a salt thereof to introduction reaction of the hydroxy protective group.

Suitable salt of the compounds (IId) and (IIe) can be referred to the acid addition salts as exemplified for the compound (I).

In case that the protective group to be introduced are lower alkyl or lower alkenyl, the reaction can be carried out by reacting the compound (IId) with lower alkylating agent or lower alkylating agent.

The lower alkylating agent or lower alkenylating agent to be used in the present reaction may include conventional one such as mono(or di)lower alkyl sulfate (e.g. dimethyl sulfate, etc.), lower alkyl(lower)alkanesulfonate (e.g. methyl methanesulfonate, etc.), halo(-lower)alkane (e.g. bromomethane, iodomethane, iodoethane, iodobutane etc.), halo(lower)alkene (e.g. iodopropene etc.) or the like.

When lower alkyl ester of an acid is used as a lower alkylating agent, the reaction is usually carried out in a solvent such as water, acetone, tetrahydrofuran, ethanol, ether, dimethylformamide or any other solvent which does not adversely influence the reaction.

The present reaction is preferably carried out in the present of a conventional base such as an inorganic base or an organic base.

The reaction temperature is not critical and the reaction is usually carried out under cooling to heating around boiling point of the solvent.

Process F

The compound (IIg) or a salt thereof can be prepared by subjecting the compound (IIf) or a salt thereof to oxidation reaction.

Suitable salt of the compound (IIf) can be referred to the acid addition salt exemplified for the compound (I).

Suitable oxidizing agent to be used in this oxidation reaction may include conventional ones such as 2,3-dichloro-5,6-dicyano-1,4-benzoquinone (DDQ), and the like.

The present oxidation is carried out with solvent such as benzene, toluene, chloroform, methylene chloride, carbon tetrachloride, diethyl ether, dimethylformamide or any other solvent which does not adversely affect the reaction, and the solvent is optionally selected according to a kind of oxidizing agent to be used.

The reaction temperature of the oxidation reaction of this process is not critical, and the reaction is carried out under cooling, at ambient temperature, under warming or under heating. The reaction temperature is optionally selected according to a kind of oxidizing agent to be used.

Process G

The compound (IIIe) or a salt thereof can be prepared by subjecting the compound (IIId) or a salt thereof to introduction reaction of the hydroxy protective group.

The present reaction can be carried out in a conventional manner.

In case that the protective group to be introduced is a silyl group, the present reaction is carried out by reacting the compound (IIId) or a salt thereof with the compound of the formula:

$$R_a—X \quad (VI)$$

wherein
$R_a$ is a trisubstituted silyl and
X is an acid residue.

Suitable acid residue may include halogen (e.g., chlorine, bromine, etc.) or the like.

The present reaction is preferably carried out in the presence of imidazole, 4-substituted imidazole, dimethylpyrazole, triazole or tetrazole.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical and the reaction is usually carried out under cooling, at ambient temperature or under warming.

Process H

The compound (IIi) or a salt thereof can be prepared by subjecting the compound (IIh) or a salt thereof to elimination reaction of the hydroxy protective group.

The present elimination reaction is carried out in accordance with a conventional method such as Process 1.

The present reaction is preferably carried out in the presence of a mild reagent such as tetra-n-butylammonium fluoride.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical and the reaction is usually carried out under cooling, at ambient temperature or under warming.

Process I

The object compound (IIk) or a salt thereof can be prepared by oxidizing the compound (IIj) or a salt thereof.

The oxidizing agent to be used in this reaction may include an inorganic peracid or a salt thereof (e.g. periodic acid, persulfuric acid, or sodium or potassium salt thereof, etc.), an organic peracid or a salt thereof (e.g. perbenzoic acid, m-chloroperbenzoic acid, performic acid, peracetic acid, chloroperacetic acid, trifluoroperacetic acid, or sodium or potassium salt thereof, etc.), ozone, hydrogen peroxide, urea-hydrogen peroxide, N-halosuccinimide (e.g. N-bromosuccinimide, N-chlorosuccinimide, etc.), hypochlorite compound (e.g. tert-butyl hypochlorite, etc.), permanganate (e.g. potassium permanganate, etc.), or any other conventional oxidizing agent which can oxidide a sulfinyl group to a sulfonyl group.

The present reaction can also be carried out in the presence of a compound comprising Group Vb or VIb metal in the Periodic Table of elements, for example, tungstic acid, molybdic acid, vanadic acid, etc., or an alkali or an alkaline earth metal salt thereof.

The present oxidation reaction is usually carried out in a conventional solvent which does not adversely influence the reaction such as water, acetic acid, chloroform, methylene chloride, acetone, methanol, ethanol or a mixture thereof.

The reaction temperature is not critical and the reaction is preferably carried out under cooling to at ambient temperature.

Particularly, the compounds (I) possessing the most potent antimicrobial activity can be represented by the following formula:

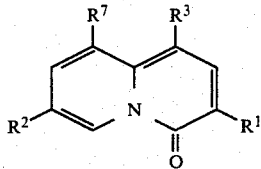

wherein $R^1$, $R^2$, $R^3$ and $R^7$ are each as defined above, and more particularly, $R^1$ is tetrazolylamido, $R^2$ and $R^7$ are each hydrogen, and $R^3$ is aryloxy or aroyl.

For the purpose of showing pharmaceutical utility of the quinolizinone compound (I), pharmaceutical test data thereof are illustrated in the following.

Test compound

N-[5-(1H-Tetrazolyl)]-4H-quinolizin-4-one-3-carboxamide (hereinafter referred to as compound A )

N-[5-(1H-Tetrazolyl)]-1-phenyl-4H-quinolizin-4-one-3-carboxamide (hereinafter referred to as compound B )

Test (A) Inhibition on stress ulcer

1 Test-Method

Sprague-Dawley rats weighing about 200 g were used. Each animal was immobilized in a small cage and put in a water bath allowing to respire. The temperature of the water bath kept at 22° C. The test compound A and B were administered orally just before the immobilization. Seven hours later, the animals were sacrificed and their stomachs were removed. The stomach was then fixed with 2% formalin. The area of ulcers was measured for each animal. The mean area (mm²) in the test animals was compared with that in the control animals.

| Treatment | No. | (2) Test Result: Ulcer index mm² | Mean ± S.E. | Inh. % |
|---|---|---|---|---|
| Control | 1 | 19 | 19.2 ± 2.8 | — |
| | 2 | 26 | | |
| | 3 | 12 | | |
| | 4 | 14 | | |
| | 5 | 25 | | |
| Compound Ⓐ 32 mg/kg | 1 | 18 | 6.2 ± 3.0 | 67.7 |
| | 2 | 5 | | |
| | 3 | 3 | | |
| | 4 | 4 | | |
| | 5 | 1 | | |
| Control | 1 | 50 | 48.4 ± 8.3 | — |
| | 2 | 52 | | |
| | 3 | 58 | | |
| | 4 | 17 | | |
| | 5 | 65 | | |
| Compound Ⓑ 32 mg/kg | 1 | 10 | 8.4 ± 1.9 | 83.7 |
| | 2 | 11 | | |
| | 3 | 3 | | |
| | 4 | 5 | | |
| | 5 | 11 | | |

(B) Effect on passive cutaneous anaphylaxis (PCA)

① Test Method

Recipient animals for PCA reactions were female Sprague-Dawley rats, 7 weeks old, 180g-200g (Nihon Kurea). Each experiment included 5 observations.

Five times crystallized ovalbumin (OVA) (Sigma Lot, 31F-8061) was used as antigen.

Female BDF1 mice, 7 weeks old (Nihon Kurea), were given a primary injection (left foot pad, s.c.) of 100 mcg OVA in 0.05 ml saline and after 20 days a booster injection by the same route. Blood was collected 28 days after the primary injection and the sera were stored at −80° C.

The animals were shared with an electric clipper in advance and prepared for Passive Cutaneous Anaphylaxis (PCA) by injecting 0.05 ml of mouse antiserum dilutions (1/16, 1/32) in each side of the dorsal skin.

They were then challenged 48 hours later with an intravenous injection of 1 ml of 0.5% Evans Blue containing 5 mg OVA. Fifty minutes later, they were killed and the lesions (diameter) measured.

A minimal skin response was one with a 5 mm or greater diameter blue spot measured on the dermal side of reflected skin. Drug activity was estimated using the following formula;

$$\% \text{ inhibition} = \left(1 - \frac{\text{drug treated (dia;mm)}}{\text{Saline treated (dia;mm)}}\right) \times 100$$

Drugs were suspended in 0.1% methyl cellulose/saline and given intravenously with the antigen.

② Test Results:

| | Dose mg/kg | Inhibition (%) Antiserum concentration | |
|---|---|---|---|
| | | 1/16 | 1/32 |
| Compound Ⓐ | 1 | 97.2 | 100 |
| | 10 | 94.5 | 100 |

The pharmaceutical composition of this invention can be used in the form of a pharmaceutical preparation, for example, in solid, semisolid or liquid form, which contains an active substance of this invention in admixture with an organic or inorganic carrier or excipient suitable for external, oral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily doses of about 0.05-5 mg of the active ingredient/kg of a human being or an animal in generally give for treating diseases, and an average, single dose of about 2.5 mg, 25 mg and 250 mg in generally administered.

The following preparations and examples are given for purpose of illustrating this invention.

PREPARATION 1

To a solution of 2-methylpyridine (7 ml) in tetrahydrofuran (140 ml) was added dropwise a solution of n-butyl lithium (49 ml of 1.59 mol solution in hexane) with ice-cooling. The resulting dark red solution was allowed to warm to ambient temperature and stirred for an hour. After cooling to $-78°$ C., a solution of diethyl ethoxymethylenemalonate (15.68 ml) in tetrahydrofuran (50 ml) was added over a period of 30 minutes. The reaction mixture was allowed to warm to $-20°$ C. and stirred for 30 minutes at $-20°$ C. Acetic acid (4.48 ml) was added. The solvent was distilled off, the residue was dissolved in ethyl acetate and washed with 10% aqueous solution of sodium bicarbonate, water and saturated aqueous sodium chloride. After drying over magnesium sulfate, the ethyl acetate extract was filtered and evaporated to give an oil (27 g). The residue was chromatographed on silica gel (Merck 70-230 mesh, 270 g) eluting with chloroform to give ethyl 3-ethoxy-2-ethoxycarbonyl-4-(2-pyridyl)butyrate (19 g) as an oil.

IR (film): 1730, 1590, 1470, 1440, 1370 $cm^{-1}$

NMR (CDCl$_3$) δ: 0.97 (t, 3H, J=8 Hz), 1.26 (t, 6H, J=8 Hz), 3.12 (d, 1H, J=8 Hz), 3.2-3.6 (m, 2H), 3.62 (d, 1H, J=8 Hz), 4.21 (q, 4H, J=8 Hz), 4.47 (q, 2H, J=8 Hz), 6.97-7.80 (m, 3H), 8.42-8.67 (m, 1H)

PREPARATION 2

A mixture of ethyl 3-ethoxy-2-ethoxycarbonyl-4-(2-pyridyl)butyrate (18.9 g), diphenyl (48.85 g) and diphenyl ether (135.8 g) was heated to 250° C. for 40 minutes. The reaction mixture was cooled to ambient temperature and chromatographed on silica gel (Merck 70-230 mesh, 620 g) eluting with hexane and then a mixture of ethanol and chloroform (1:49) to give a crude oil, which was crystallized from a mixture of ether and hexane (1:1) to give 3-ethoxycarbonyl-4H-quinolizin-4-one (11.48 g) as yellow crystal.

IR (Nujol): 1670, 1625, 1490 $cm^{-1}$

NMR (CDCl$_3$) δ: 1.42 (t, 3H, J=7 Hz), 4.42 (q, 2H, J=7 Hz), 6.62 (d, 1H, J=8 Hz), 7.02-7.38 (m, 1H), 7.53-7.68 (m, 2H), 8.33 (d, 1H, J=8 Hz), 9.23-9.47 (m, 1H)

PREPARATION 3

The following compounds were obtained according to a similar manner to that of Preparation 1.

(1) Ethyl 3-ethoxy-2-ethoxycarbonyl-4-[2-(5-ethylpyridyl)]butyrate.

IR (film): 1750, 1730 $cm^{-1}$ (2) Ethyl 3-ethoxy-2-ethoxycarbonyl-4-(2-quinolyl)-butyrate.

IR (film): 1750 (sh), 1730 $cm^{-1}$ (3) Ethyl 4-phenyl-3-ethoxy-2-ethoxycarbonyl-4-(2-pyridyl)butyrate.

IR (film): 1750 (sh), 1730 $cm^{-1}$ (4) Ethyl 3-ethoxy-2-ethoxycarbonyl-4-[2-(5-hydroxypyridyl)]butyrate.

IR (film): 2550, 1730, 1490, 1270, 1160, 1090, 1025 $cm^{-1}$

NMR (CDCl$_3$) δ: 0.97 (t, 3H, J=7 Hz), 1.25 (t, 6H, J=7 Hz), 3.07 (d, 2H, J=5 Hz), 3.20-4.77 (m, 8H), 6.47 (m, 1H), 7.07-7.37 (m, 2H), 8.17 (m, 1H)

(5) Ethyl 3-ethoxy-2-ethoxycarbonyl-4-(1-isoquinolyl)butyrate.

IR (film): 1750, 1730 $cm^{-1}$ (6) Ethyl 3-ethoxy-2-ethoxycarbonyl-3-[8-(5,6,7,8-tetrahydroquinolyl)]propionate.

IR (film): 1750, 1730 $cm^{-1}$ (7) Ethyl 3-ethoxy-2-ethoxycarbonyl-4-[2-(3-methylpyridyl)]butyrate.

IR (Nujol): 1750, 1735, 1575, 1440, 860, 790 $cm^{-1}$

NMR (CDCl$_3$) δ: 0.92 (t, 3H, J=5 Hz), 1.27 (t, 6H, J=5 Hz), 2.37 (s, 3H), 3.08-3.60 (m, 4H), 3.70 (d, 1H, J=5 Hz), 4.18 (q, 2H, J=5 Hz), 4.22 (q, 2H, J=5 Hz), 4.52 (m, 1H), 7.05 (dd, 1H, J=6 Hz and 3 Hz), 7.45 (d, 1H, J=6 Hz), 8.42 (d, 1H, J=3 Hz)

(8) Ethyl 3-ethoxy-2-carboethoxy-4-[2-(4-methylpyridyl)]butyrate.

IR (film): 1750, 1730, 1600, 1240, 1150, 1020 $cm^{-1}$

NMR (CDCl$_3$) δ: 0.97 (t, 3H, J=7 Hz), 1.27 (t, 6H, J=7 Hz), 2.32 (s, 3H), 3.10 (d, 2H, J=5.5 Hz), 3.28-3.58 (m, 2H), 4.20 (q, 3H, J=7 Hz), 4.23 (q, 3H, J=7 Hz), 6.87-7.13 (m, 2H), 8.40 (d, 1H, J=6 Hz)

(9) Ethyl 3-ethoxy-2-ethoxycarbonyl-4-[2-(6-methylpyridyl)]butyrate.

IR (film): 1650, 1630, 1590, 1580, 1270, 1150, 1090 $cm^{-1}$

NMR (CDCl$_3$) δ: 0.97 (t, 3H, J=7 Hz), 1.25 (t, 6H, J=7 Hz), 2.48 (s, 3H), 3.07 (d, 2H, J=5.5 Hz), 3.60 (q,

2H, J=7 Hz), 3.23-3.57 (m, 1H), 4.18 (q, 4H, J=7 Hz), 4.33-4.67 (m, 1H), 6.85-7.15 (m, 2H), 7.33-7.66 (m, 1H)

(10) Ethyl 3-ethoxy-2-ethoxycarbonyl-4-(2-pyridyl)pentanoate.

IR (film): 1750, 1730, 1590, 1300, 1090, 1020 cm$^{-1}$

NMR (CDCl$_3$) δ: 1.00 (t, 3H, J=7 Hz), [1.35 (t, J=7 Hz), 1.25 (t, J=7 Hz), 1.25 (s) 9H], 3.00-3.75 (m, 4H), 3.93-4.58 (m, 5H), 6.98-7.60 (m, 2H), 7.65 (m, 1H), 8.58 (m, 1H)

(11) Ethyl 3-ethoxy-2-ethoxycarbonyl-4-[2-(5-methylpyridyl)]butyrate.

IR (film): 1740, 1730, 1600, 1480, 1150, 1090, 1025 cm$^{-1}$

NMR (CDCl$_3$) δ: 1.00 (t, 3H, J=7 Hz), 1.27 (t, 6H, J=7 Hz), 2.32 (s, 3H), 3.00-3.77 (m, 4H), 4.22 (q, 3H, J=7 Hz), 4.25 (q, 3H, J=7 Hz), 7.03-7.50 (m, 2H), 8.37 (m, 1H)

(12) Ethyl 3-ethoxy-2-ethoxycarbonyl-3-[7-(6,7-dihydro-5H-cyclopenta [b] pyridyl)]propionate.

IR (film): 1750 (sh), 1730, 1590, 1580 cm$^{-1}$

NMR (CDCl$_3$) δ: 0.80 (t, 3H, J=7 Hz), 1.30 (t, 6H, J=7 Hz), 2.00-2.40 (m, 2H), 2.80-3.70 (m, 4H), 4.0 (q, 2H, J=7 Hz), 4.20 (q, 4H, J=7 Hz), 4.80 (dd, 1H, J=8 Hz and 2 Hz), 7.00-7.60 (m, 2H), 8.3-8.50 (m, 1H)

(13) Ethyl 3-ethoxy-4-methoxy-4-(2-pyridyl)-2-ethoxycarbonylbutyrate.

IR (film): 1750, 1730, 1590, 1365, 1090, 1025, 760 cm$^{-1}$

NMR (CDCl$_3$) δ: 0.78 (t, 3H, J=7 Hz), 1.25 (t, 3H, J=7 Hz), 1.28 (t, 3H, J=7 Hz), 3.33 (d, 2H, J=4 Hz), 3.60-4.60 (m, 9H ), 7.07-7.90 (m, 3H), 8.62 (m, 1H)

(14) Ethyl 3-ethoxy-4-ethoxycarbonyl-4-(2-pyridyl)butyrate.

PREPARATION 4

The following compounds were obtained according to a similar manner to that of Preparation 2.

(1) 2-Ethoxycarbonyl-1H-pyrido[1,2-a]quinolin-1-one. mp. 104°-105° C.

IR (Nujol): 1730, 1660, 1530 cm$^{-1}$

NMR (CDCl$_3$) δ: 1.43 (t, 3H, J=7 Hz), 4.43 (q, 2H, J=7 Hz), 6.40 (d, 1H, J=8 Hz), 7.0 and 7.45 (ABq, 2H, J=10 Hz), 7.50-7.70 (m, 4H), 8.20 (d, 1H, J=8 Hz), 9.70-10.0 (m, 1H)

(2) 7-Ethyl-3-ethoxycarbonyl-4H-quinolizin-4-one. mp. 81°-83° C.

IR (Nujol) : 1720, 1630 cm$^{-1}$

NMR (CDCl$_3$) δ: 1.32 (t, 3H, J=7 Hz), 1.44 (t, 3H, J=7 Hz), 2.76 (q, 2H, J=7 Hz), 4.40 (q, 2H, J=7 Hz), 6.60 (d, 1H, J=8 Hz), 7.52 (s, 2H), 8.32 (d, 1H, J=8 Hz), 9.20 (s, 1H)

(3) 1-Phenyl-3-ethoxycarbonyl-4H-quinolizin-4-one. mp. 120°-123° C.

IR (Nujol): 17.30, 1620 cm$^{-1}$

NMR (CDCl$_3$) δ: 1.36 (t, 3H, J=7 Hz), 4.38 (q, 2H, J=7 Hz), 7.04-7.76 (m, 7H), 8.32 (s, 1H), 9.48 (d, 1H, J=8 Hz)

(4) 8-Hydroxy-3-ethoxycarbonyl-4H-quinolizin-4-one. mp. 242° C. (dec.)

IR (Nujol): 3300, 3200, 1680, 1660, 1620, 1300, 1140, 960, 900 cm$^{-1}$

NMR (DMSO-d$_6$) δ: 2.27 (t, 3H, J=7 Hz), 4.23 (q, 2H, J=8 Hz), 6.13 (d, 1H, J=8 Hz), 7.58 (dd, 1H, J=2 Hz, 8 Hz), 7.90 (d, 1H, J=8 Hz), 8.07 (d, 1H, J=8 Hz), 8.82 (d, 1H, J=2 Hz)

Anal. Calcd for C$_{12}$H$_{11}$NO$_4$: C, 61.80; H, 4.75. Found: C, 62.18; H, 5.05.

(5) 3-Ethoxycarbonyl-4H-pyrido[2,1-a]isoquinolin-4-one. mp. 155° C.

IR (Nujol): 3100, 1740, 1650, 1640 cm$^{-1}$

NMR (CDCl$_3$) δ: 1.46 (t, 3H, J=7 Hz), 4.46 (q, 2H, J=7 Hz), 7.23 (d, 1H, J=8 Hz), 7.35 (d, 1H, J=8 Hz), 7.50-7.83 (m, 3H), 8.20-8.50 (m, 1H), 8.46 (d, 1H, J=8 Hz), 9.10 (d, 1H, J=8 Hz),

Anal. Calcd for C$_{16}$H$_{13}$NO$_3$: C; 71.90, H; 4.90, N; 5.24. Found : C; 71.40, H; 5.06, N; 5.17.

(6) 9-Methyl-3-ethoxycarbonyl-4H-quinolizin-4-one. mp. 125°-126° C.

IR (Nujol): 3090, 1725, 1645, 1590, 1125, 1100 cm$^{-1}$

NMR (CDCl$_3$) δ: 1.40 (t, 3H, J=7 Hz), 2.50 (s, 3H), 4.42 (q, 2H, J=7 Hz), 6.63 (d, 1H, J=9 Hz), 7.07 (t, 1H, J=7 Hz), 7.47 (d, 1H, J=7 Hz), 8.35 (d, 1H, J=9 Hz), 9.32 (d, J=7 Hz, 1H)

Anal. Calcd for C$_{13}$H$_{13}$NO$_3$: C; 67.52, H; 5.67. Found: C; 67.51, H; 5.83.

(7) 8-Methyl-3-ethoxycarbonyl-4H-quinolizin-4-one. mp. 146°-148° C.

IR (Nujol): 3060, 1720, 1660, 1640, 1245, 1155, 790 cm$^{-1}$

NMR (CDCl$_3$) δ: 1.40 (t, 3H, J=7 Hz), 2.50 (s, 3H), 4.38 (q, 2H, J=7 Hz), 6.50 (d, 1H, J=9 Hz), 7.00 (dd, 1H, J=7 Hz, 2 Hz), 7.30 (d, 1H, J=2 Hz), 8.32 (d, 1H, J=9 Hz), 9.28 (d, 1H, J=7 Hz)

Anal. Calcd for C$_{13}$H$_{13}$NO$_3$: C; 67.52, H; 5.67. Found: C; 67.38, H; 5.65.

(8) 3-Ethoxycarbonyl-6-methyl-4H-quinolizin-4-one. mp. 90°-93° C.

IR (Nujol): 1720, 1650, 1620, 1590, 1265, 1120, 1100, 795 cm$^{-1}$

NMR (CDCl$_3$) δ: 1.35 (t, 3H, J=7 Hz), 3.05 (s, 3H), 4.38 (q, 2H, J=7 Hz), 6.38 (d, 1H, J=8 Hz), 6.67 (m, 1H), 7.25 (d, 1H, J=4.5 Hz), 8.18 (d, 1H, J=8 Hz)

Anal. Calcd for C$_{13}$H$_{13}$NO$_3$: C; 67.52, H; 5.67, N; 6.07. Found: C; 67.28, H; 5.63, N; 6.03.

(9) 1-Methyl-3-ethoxycarbonyl-4H-quinolizin-4-one. mp. 142°-143° C.

IR (Nujol): 1720, 1650, 1620, 1595, 1300, 1230, 1160, 1120, 775 cm$^{-1}$

NMR (CDCl$_3$) δ: 1.42 (t, 3H, J=7 Hz), 2.40 (s, 3H), 4.43 (q, 2H, J=7 Hz), 7.20 (m, 1H), 7.62-7.80 (m, 2H), 8.25 (s, 1H), 9.47 (m, 1H)

Anal. Calcd for C$_{13}$H$_{13}$NO$_3$: C; 67.52, H; 5.67, N; 6.06. Found: C; 67.49, H; 5.94, N; 6.06.

(10) 7-Methyl-3-ethoxycarbonyl-4H-quinolizin-4-one. mp. 146°-149° C.

IR (Nujol): 1720, 1620, 1145, 1110 cm$^{-1}$

NMR (CDCl$_3$) δ: 1.42 (t, 3H, J=7 Hz), 2.45 (s, 3H), 4.43 (q, 2H, J=7 Hz), 6.62 (d, 1H, J=8 Hz), 7.47-7.57 (m, 2H), 8.33 (d, 1H, J=8 Hz), 9.23 (m, 1H)

Anal. Calcd for C$_{13}$H$_{13}$NO$_3$: C; 67.52, H; 5.62, N; 6.06. Found: C; 67.44, H; 5.85, N; 6.00.

(11) 2-Ethoxycarbonyl-8,9-dihydrocyclopenta[ij]-3H-quinolizin-3-one. mp. 149° C.

IR (Nujol): 3100, 1720, 1640, 1620, 1600, 1550, 1210, 1150 cm$^{-1}$

NMR (CDCl$_3$) δ: 1.43 (t, 3H, J=7 Hz), 3.30 (broad s, 4H), 4.30 (q, 2H, J=7 Hz), 7.0-7.30 (m, 2H), 8.30 (s, 1H), 8.86 (d, 1H, J=6 Hz)

Anal. Calcd for C$_{14}$H$_{13}$NO$_3$: C; 69.12, H; 5.39, N; 5.76. Found : C; 68.16, H; 5.47, N; 5.69.

(12) 2-Ethoxycarbonyl-9,10-dihydro-8H-benzo[ij]-3H-quinolizin-3-one. mp. 118° C.

IR (Nujol): 1680, 1620, 1600, 1220 cm$^{-1}$

NMR (CDCl$_3$) δ: 1.40 (t, 3H, J=7 Hz), 1.85-2.20 (m, 2H), 2.80-3.20 (m, 4H), 4.40 (q, 2H, J=7 Hz), 6.85-7.30 (m, 2H), 8.13 (s, 1H), 9.20 (d, 1H, J=7 Hz)

Anal. Calcd for C$_{15}$H$_{15}$NO$_3$: C; 70.02, H; 5.88, N; 5.44. Found: C; 69.78, H; 5.95, N; 5.38.

(13) 1-Methoxy-3-ethoxycarbonyl-4H-quinolizin-4-one. mp. 132°–133° C.

IR (Nujol): 1680, 1670, 1620, 1595, 1360, 1120, 1020, 770 cm$^{-1}$

NMR (CDCl$_3$) δ: 1.43 (t, 3H, J=7 Hz), 3.93 (s, 3H), 4.45 (q, 2H, J=7 Hz), 7.25 (m, 1H), 7.67 (m, 1H), 7.97–8.20 (m, 2H), 9.47 (d, 1H, J=7.5 Hz)

Anal. Calcd for C$_{13}$H$_{13}$NO$_4$: C; 63.15, H; 5.30, N; 5.66. Found: C; 62.80, H; 5.33, N; 5.63.

(14) 1-Ethoxycarbonyl-4H-quinolizin-4-one. mp. 114° C.

IR (Nujol): 1725, 1680, 1630 cm$^{-1}$.

Anal. Calcd for C$_{12}$H$_{11}$NO$_3$: C; 66.35, H; 5.10, N; 10.45. Found: C; 66.19, H; 4.81, N; 6.42.

Preparation 5

A solution of 2-ethoxycarbonyl-8,9-dihydrocyclopenta[ij]-3H-quinolizin-3-one (2.2 g) and dichlorodicyanobenzoquinone (2.26 g) in benzene (110 ml) was refluxed for two hours. The reaction mixture was cooled to 0° C. and the precipitates were filtered. The filtrate was concentrated and the residue was chromatographed on silica gel column (44 g) eluting with chloroform-methanol (100:1–10:1). Evaporation of corresponding fractions gave crude crystals which was washed with a mixture of ether and hexane to afford 2-ethoxycarbonylcyclopenta[ij]-3H-quinolizin-3-one (1.82 g), mp. 127° C.

IR (Nujol): 3100, 1680–1700 (broad), 1620, 1570, 1230, 1210 cm$^{-1}$

NMR (CDCl$_3$) δ: 1.46 (t, 3H, J=7 Hz), 4.46 (q, 2H, J=7 Hz), 6.80–7.60 (m, 3H), 8.13 (d, 1H, J=8 Hz), 8.70 (s, 1H), 9.20 (d, 1H, J=8 Hz)

Anal. Calcd for C$_{14}$H$_{11}$NO$_3$: C; 69.70, H; 4.60, N; 5.81. Found: C; 69.34, H; 4.80, N; 5.78.

PREPARATION 6

To a stirred solution of 3-ethoxycarbonyl-7-hydroxy-4H-quinolizin-4-one (4.5 g) in dry N,N-dimethylformamide (90 ml) was added sodium hydride (60% in mineral oil, 0.93 g) at room temperature and the resulting solution was kept for 30 minutes at 50° C. The reaction mixture was treated with methyl iodide (4.13 g) and stirred for 30 minute at the same temperature. The reaction mixture was poured into dilute hydrochloric acid solution and extracted with chloroform. The organic layer was washed with water, dried over anhydrous magnesium sulfate and evaporated to give an oil (12.3 g) which was applied to a silica gel column. Elution with chloroform-methanol (99:1) gave 3-ethoxycarbonyl-7-methoxy-4H-quinolizin-4-one (3.75 g), mp, 156°–158° C.

IR (Nujol): 1720, 1620, 1500, 1140, 1100 cm$^{-1}$

NMR (CDCl$_3$) δ: 1.43 (t, 3H, J=7 Hz), 3.93 (s, 3H), 4.43 (q, 2H, J=7 Hz), 6.63 (d, 1H, J=8.5 Hz), 7.23–7.70 (m, 2H), 7.28 (d, 1H, J=8.5 Hz), 9.00 (m, 1H)

Anal. Calcd for C$_{13}$H$_{13}$NO$_4$: C; 63.15, H; 5.30. Found C; 62.62, H; 5.52.

PREPARATION 7

The following compounds were obtained according to a similar manner to that of Preparation 6.

(1) 3-Ethoxycarbonyl-7-n-butoxy-4H-quinolizin-4-one. mp. 132°–133° C.

IR (Nujol): 1710, 1620, 1540, 1280, 1240, 1140, 845, 780 cm$^{-1}$

NMR (CDCl$_3$) δ: 1.00 (t, 3H, J=6 Hz), 1.43 (t, 3H, J=7.5 Hz), 1.50–2.33 (m, 4H), 4.10 (t, 2H, J=6 Hz), 4.43 (q, 2H, J=7.5 Hz), 6.63 (d, 1H, J=8 Hz), 7.23–7.67 (m, 2H), 8.28 (d, 1H, J=8 Hz), 8.97 (d, 1H, J=2 Hz)

Anal. Calcd for C$_{16}$H$_{19}$NO$_4$: C; 66.42, H; 6.62, N; 4.84. Found: C; 66.54, H; 6.52, N; 4.82.

(2) 3-Ethoxycarbonyl-7-isopropoxy-4H-quinolizin-4-one. mp. 132°–134° C.

IR (Nujol): 1725, 1625, 1240, 1140, 1100, 970, 840 cm$^{-1}$

NMR (CDCl$_3$) δ: 1.42 (d, 6H, J=6 Hz), 1.43 (t, 3H, J=7.5 Hz), 4.43 (q, 1H, J=7.5 Hz), 4.65 (m, 2H), 6.62 (d, 1H, J=8.5 Hz), 7.20–7.68 (m, 2H), 8.27 (d, 1H, J=8.5 Hz), 9.00 (d, 1H, J=2 Hz)

Anal. Calcd for C$_{15}$H$_{17}$NO$_4$: C; 65.44, H; 6.22, N; 5.09. Found: C; 65.66, H; 6.15, N; 5.10.

PREPARATION 8

A solution of ethyl 2-pyridyl acetate (6.10 ml) in ethanol (120 ml) containing sodium ethoxide (3.25 g) was refluxed for one hour. The resulting reaction mixture was treated with ethyl ethoxyacrylate (7.06 ml) and then refluxed for three days. Acetic acid (4.6 ml) was added to the reaction mixture and the solvent was evaporated to dryness. The oily residue was dissolved in ethyl acetate and washed with water, aqueous sodium bicarbonate solution. The organic layer was dried over magnesium sulfate and then evaporated to give an oily residue which was chromatographed on silica gel column. Elution with benzene-ethyl acetate (10:1) gave ethyl 3-ethoxy-4-ethoxycarbonyl-4-(2-pyridyl)butyrate (9.80 g) as an oil.

PREPARATION 9

The following compounds were obtained according to a similar manner to that of Preparation 1.

(1) Ethyl 4-phenyl-4-(2-quinolyl)-3-ethoxy-2-ethoxycarbonylbutyrate.

IR (Film): 1750, 1730, 1590, 1500, 1150, 1090, 1030 cm$^{-1}$

NMR (CDCl$_3$, δ): 0.82 (3H, t, J=7 Hz), 1.20 (3H, t, J=7 Hz), 1.28 (3H, t, J=7 Hz), 3.12 (1H, m), 3.42–4.47 (6H, m), 4.67 (1H, m), 5.25 (1H, m), 7.12–8.27 (11H, m)

(2) Ethyl 4-(2-pyridyl)-4-(1-naphthyl)-3-ethoxy-2-ethoxycarbonylbutyrate.

IR (Film): 1750, 1720, 1580, 780, 750 cm$^{-1}$

NMR (CDC$_3$, δ): 0.60 (3H, t, J=7 Hz), 1.20 (6H, t, J=7 Hz), 2.20–4.53 (8H, m), 5.33 (1H, m), 6.95–8.10 (10H, m), 8.58 (1H, m)

(3) Ethyl 4-(2-pyridyl)-4-(4-biphenylyl)-3-ethoxy-2-ethoxycarbonylbutyrate.

IR (Film): 1750, 1730, 1590, 1485, 1300, 1150, 760 cm$^{-1}$

NMR (CDCl$_3$, δ): 0.83 (3H, t, J=7 Hz), 1.33 (6H, t, J=7 Hz), 3.28 (1H, m), 3.63 (2H, q, J=7 Hz), 4.25 (4H, q, J=7 Hz), 4.50–5.30 (2H, m), 7.02–7.83 (2H, m), 8.65 (1H, m)

(4) Ethyl 4-phenoxy-4-(2-pyridyl)-3-ethoxy-2-ethoxycarbonylbutyrate.

IR (Film): 1750, 1730, 1590, 1490, 1220, 1060, 750 cm$^{-1}$

NMR (CDCl$_3$, δ): 0.80 (3H, t, J=7 Hz), 1.03 (3H, t, J=7 Hz), 1.28 (3H, t, J=7 Hz), 2.73 (1H, m), 3.17–3.70 (2H, m), 3.80–4.40 (4H, m), 4.60 (1H, m), 5.55 (1H, m), 6.80–7.03 (3H, m), 7.10–7.40 (3H, m), 7.42–7.80 (2H, m), 8.65 (1H, m)

(5) Ethyl 4-(3-tolyl)-4-(2-pyridyl)-3-ethoxy-2-ethoxycarbonylbutyrate.

IR (Film): 1750, 1730, 1600, 1590, 1100, 700 cm$^{-1}$

NMR (CCl$_4$, δ): 0.72 (3H, t, J=7 Hz), 1.07–1.45 (6H, m), 2.33 (3H, s), 3.12–3.73 (3H, m), 3.87–4.48 (5H, m), 4.95 (1H, m), 6.85–7.72 (7H, m), 8.58 (1H, m)

(6) Ethyl 4-(2-pyridyl)-4-(4-chlorophenyl)-3-ethoxy-2-ethoxycarbonylbutyrate.

IR (Film): 1750, 1730, 1590, 1490, 1090, 750 cm$^{-1}$

NMR (CDCl$_3$, δ): 0.63–0.97 (3H, m), 1.05–1.50 (6H, m), 3.03–3.82 (3H, m), 3.93–4.58 (5H, m), 4.93 (1H, m), 6.90–7.72 (7H, m), 8.53 (1H, m)

(7) Ethyl-4-(2-pyridyl)-4-(3-methoxyphenyl)-3-ethoxy-2-ethoxycarbonylbutyrate.

IR (Film): 1750, 1730, 1590, 1470, 1440, 1370, 1160, 1100, 1040, 760, 700 cm$^{-1}$ NMR (CCl$_4$, δ): 0.73 (3H, t, J=7 Hz), 1.07–1.48 (6H, m), 2.85–4.53 (8H, m), 3.72 (3H, s), 4.93 (1H, m), 6.50–7.70 (7H, m), 8.60 (1H, m)

(8) Ethyl 4-(2-tolyl)-4-(2-pyridyl)-3-ethoxy-2-ethoxycarbonylbutyrate.

IR (Film): 3060, 1740, 1720, 1590, 1440, 1090, 860, 750 cm$^{-1}$

NMR (CCl$_4$, δ): 0.70 (3H, t, J=7 Hz), 1.03–1.48 (6H, m), 2.4 (3H, m), 2.80–4.93 (9H, m), 6.80–7.60 (7H, m), 8.47 (1H, m)

(9) Ethyl 4-(2-pyridyl)-4-t-butyldimethylsiloxy-3-ethoxy-2-ethoxycarbonylbutyrate.

IR (Film): 1750, 1730, 1590, 1580 cm$^{-1}$

PREPARATION 10

The following compounds were obtained according to a similar manner to that of Preparation 2.

(1) 2-Ethoxycarbonyl-4-phenyl-1H-pyrido[1,2-a]quinolin-1-one.

mp: 158°–159° C.

IR (Nujol): 1690, 1670, 1625, 1580, 1230, 1130, 1000 cm$^{-1}$

NMR (CDCl$_3$, δ): 1.40 (3H, t, J=7 Hz), 4.42 (2H, q, J=7 Hz), 7.10–7.70 (10H, m), 8.23 (1H, s), 9.68 (1H, m)

Anal. Calcd for C$_{22}$H$_{17}$NO$_3$: C; 76.95, H; 4.99, N; 4.08. Found: C; 76.76, H; 5.05, N; 4.00.

(2) 1-(1-Naphthyl)-3-ethoxycarbonyl-4H-quinolizin-4-one.

mp: 161°–163° C.

IR (Nujol): 1690, 1665, 1590, 1270, 1240, 780, 770 cm$^{-1}$

NMR (CDCl$_3$, δ): 1.38 (3H, t, J=7 Hz), 4.43 (2H, q, J=7 Hz), 7.05–7.77 (8H, m), 7.80–8.10 (2H, m), 8.43 (1H, s), 9.58 (1H, m)

Anal. Calcd for C$_{22}$H$_{17}$NO$_3$: C; 76.95, H; 4.99, N; 4.08. Found: C; 77.14, H; 5.27, N; 3.89.

(3) 1-(4-Biphenylyl)-3-ethoxycarbonyl-4H-quinolizin-4-one.

mp: 183°–184.5° C.

IR (Nujol): 1690, 1680, 1625, 1590, 1260, 770, 740 cm$^{-1}$

NMR (CDCl$_3$, δ): 1.40 (3H, t, J=7 Hz), 4.50 (2H, q, J=7 Hz), 7.08–8.02 (12H, m), 8.43 (1H, s), 9.55 (1H, m),

Anal. Calcd for C$_{24}$H$_{19}$NO$_3$.¼H$_2$O: C; 77.09, H; 5.27, N; 3.75. Found: C; 77.04, H; 5.49, N; 3.60.

(4) 1-Phenoxy-3-ethoxycarbonyl-4H-quinolizin-4-one.

mp: 108°–109° C.

IR (Nujol): 1680, 1670, 1620, 1590, 1225, 1200, 1000 cm$^{-1}$

NMR (CDCl$_3$, δ): 1.40 (3H, t, J=7 Hz), 4.42 (2H, q, J=7 Hz), 6.78–7.48 (6H, m), 7.57–7.98 (2H, m), 8.23 (1H, s), 9.45 (1H, m)

Anal. Calcd for C$_{18}$H$_{15}$NO$_4$: C; 69.89, H; 4.89, N; 4.53. Found: C; 70.18, H; 5.03, N; 4.51.

(5) 1-(3-Tolyl)-3-ethoxycarbonyl-4H-quinolizin-4-one mp: 109°–111° C.

IR (Nujol): 1725, 1645, 1620, 1595, 1240, 770 cm$^{-1}$

NMR (CDCl$_3$, δ): 1.42 (3H, t, J=7 Hz), 2.45 (3H, s), 4.45 (2H, q, J=7 Hz), 7.08–7.48 (5H, m), 7.53–7.95 (2H, m), 8.42 (1H, s), 9.55 (1H, m)

Anal. Calcd for C$_{19}$H$_{17}$NO$_3$.1/5H$_2$O: C; 73.39, H; 5.64, N; 4.50. Found: C; 73.58, H; 5.62, N; 4.49.

(6) 1-(4-Chlorophenyl)-3-ethoxycarbonyl-4H-quinolizin-4-one.

mp: 159°–160° C.

IR (Nujol): 1680, 1670, 1490, 1295, 1260, 1240, 1130, 1020, 765 cm$^{-1}$

NMR (CDCl$_3$, δ): 1.40 (3H, t, J=7 Hz), 4.43 (2H, q, J=7 Hz),6.97–7.87 (7H, m), 8.32 (1H, s), 9.48 (1H, m)

Anal. Calcd for C$_{18}$H$_{14}$ClNO$_3$: C; 65.96, H; 4.31, N; 4.27. Found: C; 65.81, H; 4.49, N; 4.19.

(7) 1-(3-Methoxyphenyl)-3-ethoxycarbonyl-4H-quinolizin-4-one.

mp: 155°–157° C.

IR (Nujol): 3070, 1730, 1650, 1625, 1595, 1130, 1100, 780 cm$^{-1}$

NMR (CDCl$_3$, δ): 1.42 (3H, t, J=7 Hz), 3.80 (3H, s), 4.40 (2H, q, J=7 Hz), 6.85–7.93 (7H, m), 8.35 (1H, s), 9.47 (1H, m)

Anal. Calcd for C$_{19}$H$_{17}$NO$_4$.¼H$_2$O: C; 69.61, H; 5.38, N; 4.27. Found: C; 69.62, H; 5.29, N; 4.19.

(8) 1-(2-Tolyl)-3-ethoxycarbonyl-4H-quinolizin-4-one.

mp: 97°–98° C.

IR (Nujol): 1730, 1680, 1620, 1480, 1230, 1100, 785 cm$^{-1}$

NMR (CDCl$_3$, δ): 1.45 (3H, t, J=7 Hz), 2.10 (3H, s), 4.48 (2H, q, J=7 Hz), 7.18–7.83 (7H, m), 8.42 (1H, s), 9.68 (1H, m)

Anal. Calcd for C$_{19}$H$_{17}$NO$_3$: C; 74.25, H; 5.57, N; 4.56. Found: C; 74.50, H; 5.66, N; 4.50.

(9) 1-t-Butyldimethylsiloxy-3-ethoxycarbonyl-4H-quinolizin-4-one.

IR (Nujol): 1695, 1675, 1620, 1590 cm$^{-1}$

NMR (CDCl$_3$, δ): 0.2 (6H, s), 1.10 (9H, s), 1.45 (3H, t, J=7 Hz), 4.45 (2H, q, J=7 Hz), 7.10–8.0 (3H, m), 8.10 (1H, s), 9.15 (1H, d, J=8 Hz)

Anal. Calcd for C$_{18}$H$_{25}$NO$_4$Si: C; 62.22, H; 7.25, H; 4.03. Found: C; 61.97; H; 7.04, N; 4.08

PREPARATION 11

A mixture of 2-hydroxymethylpyridine (19.3 ml), t-butyldimethylsilyl chloride (36.2 g) and imidazole (27.2 g) in dimethylformamide (190 ml) was stirred for two hours at room temperature. Water was added to the reaction mixture and extracted with n-hexane. The organic layer was washed with water, dried over magnesium sulfate and then evaporated. The residue was distilled to give 2-t-butyldimethylsiloxymethylpyridine (42.30 g).

IR (Film): 1595, 1585, 1260, 1160, 1140 cm$^{-1}$

NMR (CDCl$_3$, δ): 1.0 (6H, s), 1.83 (9H, s), 4.70 (2H, s), 6.85–7.20 (1H, m), 7.25–7.70 (2H, m), 8.20–8.30 (1H, m)

PREPARATION 12

To a solution of 1-t-butyldimethylsiloxy-3-ethoxycarbonyl-4H-quinolizin-4-one (3.32 g) in tetrahydrofuran (100 ml) was added a solution of tetra-n-butylammonium fluoride (1M, 11.47 ml) at 0° C. The mixture was stirred for one hour and the solvent was distilled off. The residue was dissolved in ethyl acetate, washed with water and saturated sodium chloride solution. After drying over magnesium sulfate, the solvent was filtered and evaporated. The residue was chromatographed on silica gel eluting with chloroform to give 1-hydroxy-3-ethoxycarbonyl-4H-quinolizin-4-one (1.13 g).

mp: >250° C.
IR (Nujol): 3 100, 1690, 1650, 1620 cm$^{-1}$
NMR (DMSO-d$_6$, δ): 1.30 (3H, t, J=7 Hz), 4.25 (2H, q, J=7 Hz), 7.20–7.60 (1H, m), 7.90–8.10 (2H, m), 9.20–9.30 (1H, m), 9.60 (1H, s)
Anal. Calcd for C$_{12}$H$_{11}$NO$_4$: C; 61.80, H; 4.75, N; 6.01. Found: C; 61.11, H; 4.58, N; 5.91.

PREPARATION 13

The following compounds were obtained according to a similar manner to that of Preparation 1.

(1) Ethyl 4-phenyl-3-ethoxy-2-ethoxycarbonyl-4-(5-hydroxy-2-pyridyl)butyrate.

(2) Ethyl 3-ethoxy-2-ethoxycarbonyl-4-(N-methylanilino)-4-(2-pyridyl)butyrate.

NMR (CDCl$_3$, δ): 0.90 (3H, t, J=7.2 Hz), 1.14 (3H, t, J=7.2 Hz), 1.30 (3H, t, J=7.2 Hz), 3.03 (3H, s), 3.20–4.50 (7H, m), 5.00–5.60 (2H, m), 6.50–7.80 (8H, m), 8.57 (1H, d, J=4.4 Hz)

(3) Ethyl 3-ethoxy-2-ethoxycarbonyl-4-benzoyl-4-(2-pyridyl)butyrate.

(4) Ethyl 3-ethoxy-2-ethoxycarbonyl-4-(2-pyridyl)-4-benzylbutyrate.

IR (film): 1750, 1730, 1635, 1585, 1365, 1290, 1245, 1185, 1140, 1090, 1025, 745, 700 cm$^{-1}$
NMR (CDCl$_3$, δ): 0.98–1.50 (9H, m), 2.93–4.67 (11H, m), 6.73–7.63 (8H, m), 8.48–8.63 (1H, m)

(5) Ethyl 3-ethoxy-2-ethoxycarbonyl-4-(2-pyridyl)-4-phenylthiobutyrate.

IR (film): 1750, 1730, 1590, 1440, 1300, 1150, 1090, 1025, 760 cm$^{-1}$
NMR (CDCl$_3$, δ): 0.83–1.40 (9H, m), 3.07–4.43 (7H, m), 4.53–4.92 (2H, m), 7.0–7.73 (8H, m), 8.53 (1H, m)

PREPARATION 14

The following compounds were obtained according to a similar manner to that of Preparation 2.

(1) 3-Ethoxycarbonyl-7-hydroxy-1-phenyl-4H-quinolizin-4-one.

IR (Nujol): 1720, 1620, 1490, 1450 cm$^{-1}$
NMR (DMSO-d$_6$, δ): 1.30 (3H, t, J=7 Hz), 4.26 (2H, q, J=7 Hz), 7.46 (5H, m), 7.60–7.70 (2H, m), 7.97 (1H, s), 8.98 (1H, d, J=2 Hz)
Anal. Calcd for C$_{18}$H$_{15}$NO$_4$: C, 69.89; H, 4.89; N, 4.53. Found: C, 69.20; H, 5.30; N, 4.14.

(2) 3-Ethoxycarbonyl-1-(N-methylanilino)-4H-quinolizin-4-one.

IR (Nujol): 1690, 1680, 1600, 1510, 1380, 1235 cm$^{-1}$
NMR (DMSO-d$_6$, δ): 1.30 (3H, t, J=7 Hz), 3.30 (3H, s), 4.28 (2H, q, J=7 Hz), 6.50–8.10 (8H, m), 8.15 (1H, s), 9.40 (1H, d, J=7 Hz)
Anal. Calcd for C$_{19}$H$_{18}$N$_2$O$_3$: C, 70.79; H, 5.63; N, 8.69. Found: C, 71.00; H, 5.40; N, 8.56.

mp: 129°–132° C.

(3) 3-Ethoxycarbonyl-1-benzoyl-4H-quinolizin-4-one.

mp: 176°–178° C.

IR (Nujol): 1750, 1630, 1580, 1485, 1220, 1110, 785 cm$^{-1}$
NMR (CDCl$_3$, δ): 1.37 (3H, t, J=7 Hz), 4.38 (2H, q, J=7 Hz), 7.20–8.07 (7H, m), 8.62 (1H, s), 8.82–9.10 (1H, m), 9.42–9.67 (1H, m)
Anal. Calcd for C$_{19}$H$_{15}$NO$_4$: C, 71.02; H, 4.70; N, 4.36. Found: C, 70.76; H, 4.96; N, 4.33.

(4) 3-Ethoxycarbonyl-1-benzyl-4H-quinolizin-4-one.
mp: 102°–105° C.

IR (Nujol): 1690, 1670, 1625, 1595, 1320, 1235, 765, 725 cm$^{-1}$
NMR (CDCl$_3$, δ): 1.43 (3H, t, J=7 Hz), 4.23 (2H, s), 4.48 (2H, q, J=7 Hz), 7.02–7.42 (6H, m), 7.52–7.78 (2H, m), 8.28 (1H, s), 9.45 (1H, m)
Anal. Calcd for C$_{19}$H$_{17}$NO$_3$: C, 74.25; H, 5.57; N, 4.56. Found: C, 73.97; H, 5.72; N, 4.42.

(5) 3-Ethoxycarbonyl-1-phenylthio-4H-quinolizin-4-one.

mp: 171°–173° C.
IR (Nujol): 1740, 1660, 1625, 1575, 1280, 1220, 1140, 1120, 780, 750 cm$^{-1}$
NMR (CDCl$_3$, δ): 1.40 (3H, t, J=7 Hz), 4.42 (2H, q, J=7 Hz), 6.68–7.47 (5H, m), 7.73 (1H, m), 8.33 (1H, m), 8.72 (1H, s), 9.52 (1H, m)
Anal. Calcd for C$_{18}$H$_{15}$NO$_3$S: C, 66.44; H, 4.65; N, 4.30.
Found: C, 66.17; H, 4.69; N, 4.28.

PREPARATION 15

A mixture of 2-chloromethylpyridine (50 g), N-methylaniline (42 g), and potassium carbonate (120 g) in N,N-dimethylformamide (200 ml) was stirred for hours at 120° C. The reaction mixture was cooled to room temperature, added to water (1 l), and extracted with ether. The ether extract was washed with water and then treated with activated carbon. After drying over magnesium sulfate, the ether extract was filtered and concentrated. The residue was crystallized from isopropyl alcohol to give N-methyl-N-(2-pyridylmethyl)aniline (39 g).

mp: 60° C.
IR (Nujol): 1610, 1590, 1570, 1510, 1470, 1440, 1360 cm$^{-1}$

PREPARATION 16

To a solution of 2-methylpyridine (9.31 g) in tetrahydrofuran (200 ml) was added a 1.5M hexane solution of n-butyllithium (73.3 ml) at −20° C. The resulting solution was stirred for 30 minutes at room temperature and added to a solution of ethyl benzoate (15.02 g) in tetrahydrofuran (100 ml) at −60° C. After stirring for 2 hours at −60° C., acetic acid (15 ml) was added and the resulting mixture was allowed to warm to room temperature and concentrated in vacuo. The residue was dissolved in ethyl acetate and washed with water. The aqueous layer was reextracted with ethyl acetate and the combined extracts were washed with water, 10% aqueous solution of sodium hydrogen carbonate, and saturated aqueous sodium chloride. After drying over magnesium sulfate, the ethyl acetate extracts were filtered and evaporated. The residue (20.5 g) was chromatographed on silica gel (Merck 70–230 mesh, 308 g) eluting with chloroform to give 2-pyridylmethyl phenyl ketone (10.86 g) as an oil.

IR (Nujol): 1680, 1630, 1600, 1545, 1270, 1200, 1145, 1060, 800, 775, 690 cm$^{-1}$
NMR (CDCl$_3$, δ): 4.43 (1.5H, s), 6.02 (0.5H, s), 6.83–8.65 (9H, m)

PREPARATION 17

(1) To a solution of 5-hydroxy-2-methylpyridine (10.66 g) in tetrahydrofuran (426 ml) was added a solution of n-butyllithium (1.5M in hexane, 143 ml) at −30°∼−10° C. The reaction mixture was allowed to warm to room temperature and stirred for 1 hour at room temperature. After cooling to −78° C., cyclohexane (11.14 ml) was added dropwise and allowed to warm to 0° C. and stirred for 30 minutes at 0° C. After addition of acetic acid (24.6 ml), the solvent was distilled off and the residue was diluted with ethyl acetate, and washed successively with water, 10% aqueous sodium hydrogen carbonate and aqueous saturated sodium chloride. After drying over magnesium sulfate, the ethyl acetate extract was filtered and evaporated. The residue was washed with ethyl acetate to give 5-hydroxy-2-[(1-hydroxycyclohexyl)methyl]pyridine (11.96 g).

IR (Nujol): 1615, 1575, 1500, 1460 cm$^{-1}$

NMR (CD$_3$OD, δ): 1.20-2.00 (10H, m), 2.90 (1H, s), 4.95 (2H, s), 7.20 (2H, m), 8.05 (1H, d, J=2.0 Hz)

(2) A solution of 5-hydroxy-2-[(1-hydroxycyclohexyl)methyl]pyridine (1 g) in acetic acid (15 ml) containing sulfuric acid (5 ml) was heated to reflux for 1 hour. After cooling to room temperature, the reaction mixture was poured on an ice, basified with 10% aqueous sodium hydrogen carbonate, and extracted with ether. The combined ether extracts were washed with aqueous saturated sodium chloride, dried over magnesium sulfate, filtered, and concentrated. The residue was washed with isopropylalcohol to give 2-benzyl-5-hydroxypyridine (409 mg).

IR (Nujol): 1560, 1450, 1370, 1280 cm$^{-1}$

NMR (CDCl$_3$, δ): 4.07 (2H, s), 6.85-7.43 (7H, m), 8.08 (1H, d, J=3.0 Hz), 10.30 (1H, broad s)

PREPARATION 18

To a solution of 1-phenylthio-3-ethoxycarbonyl-4H-quinolizin-4-one (1.0 g) in acetic acid (20 ml) and chloroform (7.5 ml), was added potassium permanganate (583 mg) at 0° C. After stirring for two hours at the same temperature, the reaction mixture was allowed to warm to room temperature and stirred further for one hour. Potassium permanganate (194 mg) was added and stirred overnight. To the resulting reaction mixture was added. Saturated aqueous sodium thiosulfate solution with ice-cooling and the mixture was extracted with chloroform. After drying over magnesium sulfate, the chloroform extract was filtered and evaporated. The residue was washed with diisopropyl ether to give 1-phenylsulfonyl-3-ethoxycarbonyl-4H-quinolizin-4-one (583 mg), mp 182° C.

IR (Nujol): 1710, 1680, 1640, 1580, 1200, 1150 cm$^{-1}$

NMR (CDCl$_3$, δ): 1.45 (3H, t, J=7 Hz), 4.45 (2H, q, J=7 Hz), 7.20-8.10 (7H, m), 8.60 (1H, d, J=8 Hz), 9.18 (1H, s), 9.50 (1H, d, J=8 Hz)

Anal. Calcd for C$_{18}$H$_{15}$NO$_5$S: C, 60.50; H, 4.23; N, 3.92. Found: C, 60.44; H, 4.51; N, 3.88.

PREPARATION 19

To a solution of 3-ethoxycarbonyl-7-hydroxy-1-phenyl-4H-quinolizin-4-one (5 g) in N,N-dimethylformamide (100 ml) was added sodium hydride (63.6% in mineral oil, 732 mg) at 50° C. After stirring for 30 minutes at 50° C., n-butyliodide (2.77 ml) was added. After stirring for 1 hour at 50° C., the mixture was cooled to room temperature and added to a mixture of aqueous hydrogen chloride and an ice. The mixture was extracted with chloroform and the chloroform extract was washed with 10% aqueous sodium hydrogen carbonate and aqueous saturated sodium chloride. After drying over magnesium sulfate, the chloroform extract was filtered and concentrated in vacuo. The residue was chromatographed on silica gel (Merck 70-230 mesh, 100 g), eluting with chloroform and then 10% methanol in chloroform to give 3-ethoxycarbonyl-7-(n-butoxy)-1-phenyl-4H-quinolizin-4-one (2.37 g).

mp: 94°-95° C.

IR (Nujol): 1730, 1690, 1655, 1630, 1480 cm$^{-1}$

NMR (CDCl$_3$, δ): 0.95 (3H, t, J=5 Hz), 1.42 (3H, t, J=5 Hz), 1.30-2.10 (4H, m), 4.13 (2H, t, J=5 Hz), 4.45 (2H, q, J=5 Hz), 7.30 (1H, d, J=7 Hz), 7.42 (5H, m), 7.67 (1H, d, J=7 Hz), 8.27 (1H, s), 9.08 (1H, d, J=2 Hz)

Anal. Calcd for C$_{22}$H$_{23}$NO$_4$: C, 72.31; H, 6.34; N, 3.83. Found: C, 71.74; H, 6.39; N, 3.80.

PREPARATION 20

The following compound was obtained according to a similar manner to that of Preparation 6.

1-Allyloxy-3-ethoxycarbonyl-4H-quinolizin-4-one.

mp: 82°-84° C.

IR (Nujol): 1690, 1680, 1660, 1620, 1580, 1320, 1235, 1100, 1015, 770 cm$^{-1}$

NMR (CDCl$_3$, δ): 1.43 (3H, t, J=7 Hz), 4.42 (2H, q, J=7 Hz), 4.50-4.75 (2H, m), 5.15-5.67 (2H, m), 5.78-6.47 (1H, m), 6.97-8.32 (4H, m), 9.47 (1H, d, J=7.5 Hz)

Anal. Calcd for C$_{15}$H$_{15}$NO$_4$: C, 65.93; H, 5.53; N, 5.13. Found: C, 66.11; H, 5.36; N, 4.94.

PREPARATION 21

The following compound was obtained according to a similar manner to that of Preparation 16.

(5-Hydroxypyridin-2-yl)methyl phenyl ketone

NMR (CDCl$_3$, δ): 4.44 (2H, broad s), 6.85-7.70 (5H, m), 7.70-8.30 (3H, m), 9.34 (2H, s)

PREPARATION 22

The following compound was obtained according to a similar manner to that of Preparation 1.

Ethyl 4-benzoyl-3-ethoxy-2-ethoxycarbonyl-4-(5-hydroxypyridin-2-yl)butyrate

IR (Nujol): 1730, 1720, 1675, 1595 cm$^{-1}$

PREPARATION 23

The following compound was obtained according to a similar manner to that of Preparation 2.

1-Benzoyl-3-ethoxycarbonyl-7-hydroxy-4H-quinolizin-4-one.

IR (Nujol): 1740, 1630, 1570, 1490 cm$^{-1}$

NMR (DMSO-d$_6$, δ): 1.22 (3H, t, J=7 Hz), 4.27 (2H, q, J=7 Hz), 7.43-7.97 (6H, m), 8.22 (1H, s), 8.87 (1H, d, J=10 Hz), 8.95 (1H, d, J=2 Hz)

PREPARATION 24

The following compound was obtained according to a similar manner to that of Preparation 6.

1-Benzoyl-3-ethoxycarbonyl-7-n-butoxy-4H-quinolizin-4-one.

mp: 158°-159° C.

IR (Nujol): 1740, 1680, 1630, 1580, 1510 cm$^{-1}$

NMR (CDCl$_3$, δ): 0.98 (3H, t, J=5 Hz), 1.23 (3H, t, J=7 Hz), 1.30-2.10 (4H, m), 4.02-4.48 (4H, m), 7.37-8.18 (6H, m), 8.33 (1H, s), 8.88 (1H, d, J=10 Hz), 9.03 (1H, d, J=2 Hz)

PREPARATION 25

To a solution of sodium ethoxide (sodium, 151 mg) in ethanol (20 ml) was added ethyl pyrid-2-ylacetate (1 ml) at room temperature and the mixture was stirred for 1 hour at the same temperature. To the mixture was added diethyl ethoxymethylenemalonate (1.33 ml) at room temperature and the mixture was stirred at room temperature overnight. To the mixture was added acetic acid (0.75 ml) at room temperature and the precipitate was filtered and washed with water to give 1,3-diethoxycarbonyl-4H-quinolizin-4-one (896 mg). mp: 130°–131° C.

IR (Nujol): 1680, 1625, 1585 cm$^{-1}$

NMR (CDCl$_3$, δ): 1.40 (6H, t), 4.20–4.55 (4H, m), 7.20–7.46 (1H, m), 7.72–8.00 (1H, m), 9.15 (1H, s), 9.27–9.64 (2H, m).

EXAMPLE 1

To a solution of 3-ethoxycarbonyl-4H-quinolizin-4-one (2.17 g) in methanol (65.2 ml) was added dropwise 6 N aqueous sodium hydroxide (6.5 ml) at room temperature. After stirring for 20 minutes, water (10 ml) was added. After stirring for 20 minutes, water (30 ml) was also added. After stirring for an hour, the reaction mixture was acidified to pH 3 with 4N aqueous hydrochloric acid. The precipitate was filtered and washed with water to give 4H-quinolizin-4-one-3-carboxylic acid (1.75 g) as pale yellow crystal. mp 233° C.

IR (Nujol): 1730, 1610, 1585, 1320 cm$^{-1}$

NMR (DMSO-d$_6$) δ: 7.26 (d, 1H, J=9 Hz), 7.50–7.95 (m, 1H), 8.00–8.20 (m, 2H), 8.41 (d, 1H, J=9 Hz), 9.20–9.40 (m, 1H)

EXAMPLE 2

To a suspension of 4H-quinolizin-4-one-3-carboxylic acid (1.69 g) in N,N-dimethylformamide (16.9 ml) was added 1,1'-carbonyldiimidazole (2.17 g) at ambient temperature. The resulting suspension was heated to 100° C. for 30 minutes and 5-amino-1H-tetrazole (1.06 g) was added at 100° C. After stirring for 20 minutes at 100° C., the reaction mixture was cooled to 0° C. The precipitate was filtered and washed with pre-cooled N,N-dimethylformamide and then ether to give N-[5-(1H-tetrazolyl)]-4H-quinolizin-4-one-3-carboxamide (2.0 g) as yellow solid. mp >260° C.

IR (Nujol): 3200, 1660, 1620, 1500, 1310 cm$^{-1}$

NMR (CF$_3$COOH) δ: 7.42 (d, 1H, J=8 Hz), 7.68–7.88 (m, 1H), 7.98–8.29 (m, 2H), 8.72 (d, 1H, J=8 Hz), 9.48 (d, 1H, J=8 Hz)

Analysis Calcd. for C$_{11}$H$_8$O$_2$N$_6$: C; 51.56, H; 3.15, N; 32.80. Found: C; 51.70, H; 3.22, N; 32.99.

EXAMPLE 3

The following compounds were obtained according to a similar manner to that of Example 1.

(1) 7-Ethyl-4H-quinolizin-4-one-3-carboxylic acid. mp. 193°–195° C.

IR (Nujol): 3100, 1725, 1700, 1605 cm$^{-1}$

NMR (CF$_3$COOH) δ: 1.52 (t, 3H, J=8 Hz), 3.12 (q, 2H, J=8 Hz), 7.92 (d, 1H, J=9 Hz), 8.32 (s, 2H), 8.73 (d, 1H, J=9 Hz), 9.30 (m. 1H).

Analysis Calcd. for C$_{12}$H$_{11}$NO$_3$: C; 66.35, H; 5.10, N; 6.45. Found: C; 66.40, H; 5.14, N; 6.46.

(2) 1-Phenyl-4H-quinolizin-4-one-3-carboxylic acid. mp. 198° C.

IR (Nujol): 3315, 1740, 1620 cm$^{-1}$

NMR (CF$_3$COOH) δ: 7.32–7.82 (m, 5H), 7.92–8.23 (m, 1H), 8.25–8.52 (m, 2H), 8.70 (s, 1H), 9.48–9.72 (m, 1H),

Analysis Calcd. for C$_{16}$H$_{11}$NO$_3$.5/4H$_2$O: C; 66.78, H; 4.64, N; 4.87. Found: C; 66.89, H; 4.22, N; 4.59.

(3) 1H-Pyrido[1,2-a]quinolin-1-one-2-carboxylic acid. mp. 258°–260° C.

IR (Nujol): 2500, 1720 cm$^{-1}$

NMR (CF$_3$COOH) δ: 7.75–8.33 (m, 5H), 8.43 (d, 1H, J=9 Hz), 8.92 (d, 1H, J=8.5 Hz), 9.73 (m, 1H)

Anal. Calcd for C$_{14}$H$_9$NO$_3$.1/10H$_2$O: C; 69.76, H; 3.85, N; 5.81. Found: C; 69.87, H; 4.13, N; 5.94.

(4) 7-Hydroxy-4H-quinolizin-4-one-3-carboxylic acid. mp. >270° C.

IR (Nujol): 3120, 2690, 1690, 1590 cm$^{-1}$

NMR (CF$_3$COOH) δ: 7.87 (d, 1H, J=8.5 Hz), 8.07–8.42 (m, 2H), 8.58 (d, 1H, J=8.5 Hz), 9.07 (m, 1H)

Anal. Calcd for C$_{10}$H$_7$NO$_4$.¼H$_2$O: C; 57.28, H; 3.61, N; 6.68. Found: C; 57.51, H; 3.60, N; 6.75.

(5) 4H-Pyrido[2,1-a]isoquinolin-4-one-3-carboxylic acid. mp. >250° C.

IR (Nujol): 3100, 1730, 1640, 1620 cm$^{-1}$

NMR (CF$_3$COOH) δ: 8.0–8.40 (m, 4H), 8.80–9.30 (m, 4H)

Anal. Calcd for C$_{14}$H$_9$NO$_3$: C; 70.29, H; 3.79, N; 5.85. Found: C; 70.43, H; 4.15, N; 5.89.

(6) 9,10-Dihydro-8H-benzo[ij]-3H-quinolizin-3-one-2-carboxylic acid. mp. 254° C.

IR (Nujol): 3200, 1710, 1610, 1590 cm$^{-1}$

NMR (DMSO-d$_6$) δ: 1.80–2.30 (m, 2H), 2.70–3.20 (m, 6H), 7.30–7.85 (m, 2H), 8.10 (s, 1H), 9.10 (d, 1H, J=7 Hz), 14.30 (s, 1H)

Anal. Calcd for C$_{13}$H$_{11}$NO$_3$: C; 68.11, H; 4.84, N; 6.11. Found: C; 68.21, H; 5.12, N; 6.07.

(7) 7-Methoxy-4H-quinolizin-4-one-3-carboxylic acid. mp. 215°–216° C.

IR (Nujol): 3150, 3100, 1700, 1610, 1590 cm$^{-1}$

NMR (CF$_3$COOH) δ: 4.18 (s, 3H), 7.88 (d, 1H, J=8.5 Hz), 8.10–8.47 (m, 2H), 8.67 (d, 1H, J=8.5 Hz), 8.88 (m, 1H)

Anal Calcd for C$_{11}$H$_9$NO$_4$: C; 60.27, H; 4.14, N; 6.39. Found: C; 59.90, H; 4.38, N; 6.48.

(8) 9-Methyl-4H-quinolizin-4-one-3-carboxylic acid. mp. 259°–260° C.

IR (Nujol): 3100, 3020, 1740, 1610, 1590, 1120, 780 cm$^{-1}$

NMR (DMSO-d$_6$) δ: 2.92 (s, 3H), 7.90 (d, 1H, J=7.5 Hz), 8.07 (d, 1H, J=9.5 Hz), 8.05–8.38 (m, 1H), 8.82 (d, 1H, J=9.5 Hz), 9.42 (d, 1H, J=7.5 Hz)

Anal. Calcd for C$_{11}$H$_9$NO$_3$: C; 65.02, H; 4.46, N; 6.89. Found: C; 64.92, H; 4.76, N; 6.89.

(9) 8-Methyl-4H-quinolizin-4-one-3-carboxylic acid. mp. 228°–230° C.

IR (Nujol): 3090, 3030, 2700, 1630, 1620, 1580, 785 cm$^{-1}$

NMR (CF$_3$COOH) δ: 2.82 (s, 3H), 7.82 (d, 1H, J=9 Hz), 7.92 (dd, 1H, J=7 Hz, 2 Hz), 8.17 (d, 1H, J=2 Hz), 8.68 (d, 1H, J=9 Hz), 9.37 (d, 1H, J=7 Hz)

Anal. Calcd for C$_{11}$H$_9$NO$_3$: C; 65.02, H; 4.46, N; 6.89. Found: C; 64.88, H; 4.79, N; 6.85.

(10) 6-Methyl-4H-quinolizin-4-one-3-carboxylic acid. mp. 185°–187° C.

IR (Nujol): 3100, 2700, 1720, 1615, 1595, 1295, 1040, 800 cm$^{-1}$

NMR (CF$_3$COOH) δ: 3.45 (s, 3H), 7.82 (d, 1H, J=9 Hz), 7.58–7.97 (m, 1H), 8.10–8.30 (m, 2H), 8.68 (d, 1H, J=9 Hz)

Anal. Calcd for C$_{11}$H$_9$NO$_3$: C; 65.02, H; 4.46, N; 6.89. Found: C; 64.60, H; 4.52, N; 6.91.

(11) 1-Methyl-4H-quinolizin-4-one-3-carboxylic acid. mp. 258°–260° C.

IR (Nujol): 1740, 1610, 1450, 780 cm$^{-1}$

NMR (CF$_3$COOH) δ: 2.87 (s, 3H), 8.15 (m, 1H), 8.35–8.77 (m, 3H), 9.66 (m, 1H)

Anal Calcd for C$_{11}$H$_9$NO$_3$: C; 65.02, H; 4.46, N; 6.89. Found: C; 64.70, H; 4.56, N; 6.86.

(12) Cyclopenta[ij]-3H-quinolizin-3-one-2-carboxylic acid. mp >250° C.

IR (Nujol): 1730, 1620, 1590 cm$^{-1}$

Anal. Calcd for $C_{12}H_7NO_3$: C; 67.61, H; 3.31, N; 6.57. Found: C; 67.72, H; 3.37, N; 6.59.

(13) 7-Methyl-4H-quinolizin-4-one-3-carboxylic acid. mp. 222°–224° C.

IR (Nujol): 1720, 1600, 1590, 1320, 1125, 1110, 840 cm$^{-1}$

NMR (CF$_3$COOH) δ: 2.77 (s, 3H), 7.93 (d, 1H, J=9 Hz), 8.22–8.38 (m, 2H), 8.73 (d, 1H, J=9 Hz), 9.32(s, 1H)

Anal. Calcd for $C_{11}H_9NO_3$: C; 65.02, H; 4.46, N; 6.89. Found: C; 65.04, H; 4.31, N; 6.91.

(14) 4H-Quinolizin-4-one-1-carboxylic acid. mp. >250° C.

IR (Nujol): 1695, 1650 cm$^{-1}$

MR (DMSO-d$_6$) δ: 6.46 (d, 1H, J=10 Hz), 7.30–8.20 (m, 2H), 8.41 (d, 1H, J=10 Hz), 9.20–9.40 (m, 2H)

Anal. Calcd for $C_{10}H_7NO_3$: C; 63.49, H; 3.73, N; 7.40. Found: C; 63.50, H; 3.81, N; 7.53.

(15) 1-Methoxy-4H-quinolizin-4-one-3-carboxylic acid. mp. 259°–261° C.

IR (Nujol): 3100, 1630, 1620, 1580, 1100, 1070, 780 cm$^{-1}$

NMR (CF$_3$COOH) δ: 4.27 (s, 3H), 8.00–8.67 (m, 3H), 8.90 (m, 1H), 9.52 (d, 1H, J=7.5 Hz)

Anal. Calcd for $C_{11}H_9NO_4$: C; 60.28, H; 4.14, N; 6.39. Found: C; 59.64, H; 4.15, N; 6.30.

(16) 7-n-Butoxy-4H-quinolizin-4-one-3-carboxylic acid. mp. 120°–122° C.

IR (Nujol): 1725, 1600, 1590, 1320, 1070, 1000 cm$^{-1}$

NMR (CF$_3$COOH) δ: 1.07 (t, 3H, J=6 Hz), 1.30–2.20 (m, 4H), 4.40 (t, 2H, J=6 Hz), 7.90 (d, 1H, J=9.5 Hz), 8.13–8.43 (m, 2H), 8.67 (d, 1H, J=9.5 Hz), 8.93 (d, 1H, J=2 Hz)

Anal. Calcd for $C_{14}H_{15}NO_4$: C; 64.36, H; 5.79, N; 5.36. Found: C; 64.46, H; 5.80, N; 5.31.

(17) 7-Isopropoxy-4H-quinolizin-4-one-3-carboxylic acid. mp. 218°–219° C.

IR (Nujol): 3140, 3090, 1720, 1620, 1120, 1060, 1000, 780 cm$^{-1}$

NMR (CF$_3$COOH) δ: 1.67 (d, 6H, J=6 Hz), 4.97 (1H, J=6 Hz), 7.88 (d, 1H, J=9 Hz), 8.10–8.43 (m, 4H), 8.63 (d, 1H, J=9 Hz), 8.90 (d, 1H, J=2 Hz)

Anal. Calcd for $C_{13}H_{13}NO_4$: C; 63.15, H; 5.30, N; 5.66. Found: C; 63.28, H; 5.18, N; 5.65.

EXAMPLE 4

The following compounds were obtained according to a similar manner to that of Example 2.

(1) N-[3-(4H-1,2,4-Triazolyl)]-4H-quinolizin-4-one 3-carboxamide. mp. >250° C.

IR (Nujol): 3400, 3300, 1700, 1660, 1650, 1620 cm$^{-1}$

NMR (CF$_3$COOH) δ: 7.90–9.60 (m, 7H)

Anal. Calcd for $C_{12}H_9N_5O_2$: C; 56.47, H; 3.55, N; 27.44. Found: C; 56.83, H; 3.79, N; 27.50.

(2) N-[5-(1H-Tetrazolyl)]-9-methyl-4H-quinolizin-4-one-3-carboxamide. mp. >270° C.

IR (Nujol): 3200, 3100, 3080, 1660, 1620, 1590, 790 cm$^{-1}$

NMR (CF$_3$COOH) δ: 2.80 (s, 3H), 7.50–7.87 (m, 2H), 8.08 (d, 1H, J=7 Hz), 8.78 (d, 1H, J=9 Hz), 9.43 (d, 1H, J=7 Hz)

Anal. Calcd for $C_{12}H_{10}N_6O_2$: C; 53.33, H; 3.73, N; 35.10. Found: C; 55.28, H; 3.88, N; 31.35.

(3) N-[5-(1H-Tetrazolyl)]-7-ethyl-4H-quinolizin-4-one-3-carboxamide. mp. >250° C.

IR (Nujol): 3200, 1660, 1640, 1620, 1590, 1490 cm$^{-1}$

NMR (CF$_3$COOH) δ: 1.50 (t, 3H, J=7 Hz), 3.05 (q, 2H, J=7.5 Hz), 7.45 (d, 1H, J=9 Hz), 8.08 (s, 2H), 8.68 (d, 1H, J=9 Hz), 9.33 (m, 1H)

Anal. Calcd for $C_{13}H_{12}N_6O_2$: C; 54.93, H; 4.25, N; 29.56. Found: C; 55.32; H; 4.32, N; 29.72.

(4) N-[5-(1H-Tetrazolyl)]-1-phenyl-4H-quinolizin-4-one-3-carboxamide. mp. >270° C.

IR (Nujol): 3180, 3100, 1680, 1620, 1490 cm$^{-1}$

NMR (CF$_3$COOH) δ: 7.27–8.02 (m, 6H), 8.05–8.35 (m, 2H), 8.70 (s, 1H), 9.48–9.75 (m, 1H)

Anal. Calcd for $C_{17}H_{12}N_6O_2$: C; 61.44, H; 3.64, N; 25.29. Found: C; 61.21, H; 3.80, N; 24.83.

(5) N-[5-(1H-Tetrazolyl)]-1H-pyrido[1,2-a]-quinolin-1-one-2-carboxamide. mp. >270° C.

IR (Nujol): 3200, 1670, 1610, 1580, 1530, 1480 cm$^{-1}$

NMR (CF$_3$COOH) δ: 7.32 (d, 1H, J=9 Hz), 7.48–8.33 (m, 5H), 8.83 (d, 1H, J=8 Hz), 9.63 (m, 1H)

Anal. Calcd for $C_{15}H_{10}N_6O_2$: C; 58.82; H; 3.29, N; 27.44. Found: C; 59.16, H; 3.42, N; 27.29.

(6) N-[5-(1H-Tetrazolyl)]-7-hydroxy-4H-quinolizin-4-one-3-carboxamide. mp. >270° C.

IR (Nujol): 3120, 3090, 2530, 1670, 1640, 1540, 980 cm$^{-1}$

NMR (CF$_3$COOH) δ: 7.73–7.70 (m, 2H), 8.03 (m, 1H), 8.67 (m, 1H), 9.15 (m, 1H)

Anal. Calcd for $C_{11}H_8N_6O_3$: C; 49.06, H; 3.32, N; 32.11. Found: C; 48.56, H; 3.47, N; 32.66.

(7) N-[5-(1H-Tetrazolyl)]-4H-pyrido[2,1-a]-isoquinolin-4-one-3-carboxamide. mp. >250° C.

IR (Nujol): 3200, 1660, 1640, 1620 cm$^{-1}$

Anal. Calcd for $C_{15}H_{10}N_6O_2$: C; 58.82, H; 3.29, N; 27.44. Found: C; 59.12, H; 3.57, N; 27.86.

(8) N-[5-(1H-Tetrazolyl)]-9,10-dihydro-8H-benzo[ij]-3H-quinolizin-3-one-2-carboxamide. mp. >250° C.

IR (Nujol): 3200, 1660, 1640, 1620, 1600 cm$^{-1}$

NMR (CF$_3$COOH) δ: 2.00–2.50 (m, 2H), 3.00–3.60 (m, 4H), 7.70–8.20 (m, 2H), 8.55 (s, 1H), 9.40 (d, 1H, J=7 Hz)

Anal Calcd for $C_{14}H_{12}N_6O_2$: C; 56.75, H; 4.08, N; 28.36. Found: C; 56.86, H; 4.27, N; 28.58.

(9) N-[5-(1H-Tetrazolyl)]-7-methoxy-4H-quinolizin-4-one-3-carboxamide. mp. >270° C.

IR (Nujol): 3200, 3100, 1680, 1650, 1610 cm$^{-1}$

NMR (CF$_3$COOH) δ: 4.13 (s, 3H), 7.42 (d, 1H, J=9 Hz), 7.73–8.17 (m, 2H), 8.58 (d, 1H, J=9 Hz), 8.92 (m, 1H)

Anal. Calcd for $C_{12}H_{10}N_6O_3$: C; 50.35, H; 3.52, N; 29.36. Found: C; 50.54, H; 3.55, N; 29.63.

(10) N-(2-Thiazolyl)-4H-quinolizin-4-one-3-carboxamide. mp. 240° C.

IR (Nujol): 3100, 1665, 1620, 1490, 1320 cm$^{-1}$

NMR (CF$_3$COOH) δ: 7.30–7.90 (m, 4H), 8.03–8.47 (m, 2H), 8.75 (d, 1H, J=9 Hz), 9.42 (d, 1H, J=7 Hz)

Anal. Calcd for $C_{13}H_9N_3OS$: C; 57.56, H; 3.34, N; 15.49. Found: C; 57.25, H; 3.77, N; 15.24.

(11) N-(2-Hydroxyphenyl)-4H-quinolizin-4-one-3-carboxamide. mp. 247° C.

IR (Nujol): 1650, 1630, 1600 cm$^{-1}$

NMR (CDCl$_3$) δ: 6.80–7.50 (m, 5H), 7.70 (d, 2H, J=7 Hz), 8.76 (d, 1H, J=8 Hz), 9.40 (d, 1H, J=8 Hz), 10.10 (s, 1H)

Anal. Calcd for $C_{16}H_{12}N_2O_3$: C; 68.57, H; 4.32, N; 9.99. Found: C; 68.04, H; 4.48, N; 10.11.

(12) N-(2-Pyrimidinyl)-4H-quinolizin-4-one-3-carboxamide. mp. 218° C.

IR (Nujol): 1690, 1650, 1620 cm$^{-1}$

NMR (DMSO-d$_6$) δ: 7.10–8.20 (m, 5H), 8.50–8.80 (m, 3H), 9.20–9.40 (m, 1H)

Anal. Calcd for $C_{14}H_{10}N_4O_2$: C; 63.15, H; 3.79, N; 21.04. Found: C; 61.20, H; 4.19, N; 20.76.

(13) N-[5-(1H-Tetrazolyl)]-8-methyl-4H-quinolizin-4-one-3-carboxamide. mp. >270° C.

IR (Nujol): 3200, 3150, 1660, 1635, 1590, 780 cm$^{-1}$

NMR (CF₃COOH) δ: 2.73 (s, 3H), 7.35 (d, 1H, J=9 Hz), 7.65 (dd, 1H, J=7 Hz, 2 Hz), 7.88 (d, 1H, J=2 Hz), 8.65 (d, 1H, J=9 Hz), 9.38 (d, 1H, J=7 Hz)

Anal. Calcd for C₁₂H₁₀N₆O₂: C; 53.33, H; 3.73, N; 31.10. Found: C; 54.03, H; 3.84; N; 30.38.

(14) N-[5-(1H-Tetrazolyl)]-6-methyl-4H-quinolizin-4-one-3-carboxamide. mp. >270° C.

IR (Nujol): 3200, 1660, 1620, 1590, 1030, 820, 790 cm⁻¹

NMR (CF₃COOH) δ: 3.33 (s, 3H), 7.37 (d, 1H, J=9 Hz), 7.37–7.62 (m, 1H), 7.87–8.07 (m, 2H), 8.60 (d, 1H, J=9 Hz)

Anal. Calcd for C₁₂H₁₀N₆O₂: C; 53.33, H; 3.73, N; 31.10. Found: C; 53.63, H; 3.92, N; 31.42.

(15) N-[5-(1H-Tetrazolyl)]-1-methyl-4H-quinolizin-4-one-3-carboxamide. mp. >270° C.

IR (Nujol): 3180, 1665, 1640, 1620, 1595, 1500, 1040, 1020, 770 cm⁻¹

NMR (CF₃COOH) δ: 2.77 (s, 3H), 7.83–8.10 (m, 1H), 8.38 (d, 2H, J=3 Hz), 8.72 (s, 1H), 9.65 (d, 1H, J=6 Hz)

Anal. Calcd for C₁₂H₁₀N₆O₂: C; 53.55, H; 3.73, N; 31.10. Found: C; 53.71, H; 4.04, N; 31.03.

(16) N-[5-(1H-Tetrazolyl)]-7-methyl-4H-quinolizin-4-one-3-carboxamide. mp. >270° C.

IR (Nujol): 3200, 1670, 1610, 1580, 1500, 1310, 1060, 1040, 840 cm⁻¹

NMR (CF₃COOH) δ: 2.73 (s, 3H), 7.47 (d, 1H, J=9 Hz), 8.03–8.50 (m, 2H), 8.70 (d, 1H, J=9 Hz), 9.33 (s, 1H)

Anal. Calcd for C₁₂H₁₀N₆O₂: C; 53.33, H; 3.73, N; 31.10. Found: C; 53.61, H; 3.69, N; 31.34.

(17) N-[6-(1,2,4-Triazinyl)]-4H-quinolizin-4-one-3-carboxamide. mp. 263° C. (dec.)

IR (Nujol): 3100, 1690, 1620, 1580, 1520, 1500, 1040 cm⁻¹

NMR (CF₃COOH) δ: 7.33 (d, 1H, J=9 Hz), 7.60–8.23 (m, 3H), 8.72 (d, 1H, J=9 Hz), 9.10–9.17 (m, 1H), 9.27–9.68 (m, 2H)

Anal. Calcd for C₁₃H₉N₅O₂·½H₂O: C; 57.51, H; 3.59, N; 25.97. Found: C; 57.51, H; 3.52, N; 25.77.

(18) N-pyrazinyl-4H-quinolizin-4-one-3-carboxamide. mp. >250° C.

IR (Nujol): 3400, 1675, 1620, 1580, 1520, 1500, 1400, 1320, 780 cm⁻¹

NMR (CF₃COOH) δ: 7.43 (d, 1H, J=9.5 Hz), 7.78 (m, 1H), 8.00–8.23 (m, 2H), 8.77 (d, 9.5 Hz), 8.83 (d, J=7.5 Hz), 8.78–8.98 (m, 3H), 9.55 (d, 1H, J=7.5 Hz), 9.82 (s, 1H)

Anal. Calcd for C₁₄H₁₀N₄O₂·H₂O: C; 59.15, H; 4.25, N; 19.71. Found: C; 59.58, H; 4.03, N; 19.99.

(19) N-[5-(1H-Tetrazolyl)]-cyclopenta[ij]-3H-quinolizin-3-one-2-carboxamide. mp. >250° C.

IR (Nujol): 3200, 3100, 1660, 1620, 1600 cm⁻¹

NMR (CF₃COOH) δ: 7.10–9.50 (m, 6H)

Anal. Calcd for C₁₃H₈N₆O₂: C; 55.72, H; 2.88, N; 29.99. Found: C; 55.95, H; 3.01, N; 29.64.

(20) N-(2-Pyridyl)-4H-quinolizin-4-one-3-carboxamide. mp. 228°–230° C.

(21) N-[5-(1H-Tetrazolyl)]-4H-quinolizin-4-one-1carboxamide. mp. >250° C.

IR (Nujol): 1690 (sh), 1660, 1620 cm⁻¹

NMR (CF₃COOH) δ: 7.40–9.80 (m, 6H)

Anal. Calcd for C₁₁H₈N₆O₂: C; 51.56, H; 3.15, N; 32.80. Found: C; 51.71, H; 3.43, N; 32.41.

(22) N-[6-(3-Chloropyridazinyl)]-4H-quinolizin-4-one-3-carboxamide. mp. >250° C.

IR (Nujol): 3100, 1680, 1620, 1580, 1510, 1070, 780 cm⁻¹

NMR (CF₃COOH) δ: 7.38 (d, 1H, J=9 Hz), 7.63–8.50 (m, 5H), 8.77 (d, 1H, J=9 Hz), 9.48 (m, 1H).

Anal. Calcd for C₁₄H₉ClN₄O₂: C; 55.92, H; 3.02, N; 18.63. Found: C; 55.65, H; 3.15, N; 19.14.

(23) N-[5-(1H-Tetrazolyl)]-1-methoxy-4H-quinolizin-4-one-3-carboxamide. mp. >270° C.

IR (Nujol): 3200, 1660, 1650, 1620, 1290, 1015, 775 cm⁻¹

NMR (CF₃COOH) δ: 4.33 (s, 3H), 8.13 (m, 1H), 8.33 (s, 1H), 8.43–9.02 (m, 2H), 9.62 (d, 1H, J=7.5 Hz)

Anal. Calcd for C₁₂H₁₀N₆O₃: C; 50.35, H; 3.52, N; 29.36. Found: C; 50.46, H; 3.45, N; 29.39.

(24) N-[2-(4,6-Dimethylpyrimidinyl)]-4H-quinolizin-4-one-3-carboxamide. mp. 217°–218° C.

IR (Nujol): 3460, 3120, 1690, 1650, 1620, 1060, 790 cm⁻¹

NMR (CF₃COOH) δ: 2.87 (s, 6H), 7.38 (d, 1H, J=9 Hz), 7.47–8.32 (m, 4H), 8.75 (d, 1H, J=9 Hz), 9.63 (d, 1H, J=7.5 Hz)

Anal. Calcd for C₁₆H₁₄N₄O₂·⅓H₂O: C; 63.99, H; 4.92, N; 19.04. Found: C; 63.99, H; 4.92, N; 18.66.

(25) N-[5-(1H-Tetrazolyl)]-7-n-butoxy-4H-quinolizin-4-one-3-carboxamide. mp. >270° C.

IR (Nujol): 3200, 1665, 1640, 1625, 1590, 1000, 850, 780 cm⁻¹

NMR (CF₃COOH) δ: 1.10 (t, 3H, J=6.5 Hz), 1.37–2.3 (m, 4H), 4.38 (t, 2H, J=6.5 Hz), 7.53 (d, 1H, J=8.5 Hz), 7.97–8.28 (m, 2H), 8.67 (d, 1H, J=8.5 Hz), 9.03 (s, 1H)

Anal. Calcd for C₁₅H₁₆N₆O₃: C; 54.88, H; 4.91, N; 26.00. Found: C; 55.14, H; 4.89, N; 25.83.

(26) N-[5-(1H-Tetrazolyl)]-7-isopropoxy-4H-quinolizin-4-one-3-carboxamide. mp. >270° C.

IR (Nujol): 3200, 1680, 1650, 1620, 1500, 1310, 780 cm⁻¹

NMR (CF₃COOH) δ: 1.77 (d, 6H, J=6 Hz), 5.12 (sept, 1H, J=6 Hz), 7.67 (d, 1H, J=8.5 Hz), 8.02–8.37 (m, 2H), 8.80 (d, 1H, J=8.5 Hz), 9.20 (s, 1H)

Anal. Calcd for C₁₄H₁₄N₆O₃: C; 53.50, H; 4.49, N; 26.74. Found: C; 53.73, H; 4.41, N; 27.04.

EXAMPLE 5

(1) To a suspension of 4H-quinolizin-4-one-3-carboxylic acid (2.27 g) in dry N,N-dimethylformamide (22.7 ml) was added 1,1'-carbonyldiimidazole (2.92 g). The resulting suspension was heated to 100° C. and kept for 30 minutes. After cooling to room temperature the resulting solution was treated with dry ammonia and stirred for 20 minutes. The crystals separated was collected by filtration and washed with water to give 4H-quinolizin-4-one-3-carboxamide (1.94 g). mp. 230°–232° C.

IR (Nujol): 3350, 3120, 1660, 1630 cm⁻¹

NMR (CF₃COOH) δ: 7.58 (d, 1H, J=9 Hz), 7.75–8.07 (m, 1H), 8.12 (m, 2H), 8.60 (d, 1H, J=9 Hz) and 9.52 (d, 1H, J=7 Hz).

Anal. Calcd for C₁₀H₈N₂O₂: C; 63.83, H; 4.28, N; 14.89. Found: C; 63.96, H, 4.43, N; 14.90.

(2) A mixture of 4H-quinolizin-4-one-3-carboxamide (1.0 g) and phosphorus oxychloride (50 ml) was refluxed for one hour. The reaction mixture was concentrated under reduced pressure and the residue was dissolved in aqueous sodium bicarbonate solution and chloroform. The chloroform extract was washed with water, dried over anhydrous magnesium sulfate and then evaporated. The residue was chromatographed on silica gel (30 g) eluting with chloroform-methanol (50:1) to give 3-cyano-4H-quinolizin-4-one, which on recrystallization from ether gave crystals (800 mg), mp. 198°-200° C.

IR (Nujol): 2420, 1680, 1620 cm$^{-1}$

NMR (DMSO-d$_6$) δ: 6.93 (d, 1H, J=8 Hz), 7.30-7.60 (m,1H), 7.86-8.20 (m, 3H), 9.13 (d, 1H, J=8 Hz)

(3) To a solution of 3-cyano-4H-quinolizin-4-one (1.20 g) in a mixture of pyridine (50 ml) and triethylamine (30 ml) was bubbled hydrogen sulfide gas over a period of 30 minutes at room temperature. The resulting mixture was allowed to stand at ambient temperature for 3 days. The solvent was distilled off and the residue was washed with a hot mixture of chloroform and methanol (1: 1) and filtered. The filtrate was concentrated and the residue was washed again with a hot mixture of chloroform and methanol (9:1) and filtered. The filtered cake was washed well with a mixture of chloroform and methanol (9:1) to give 4H-quinolizin-4-one-3-thiocarboxamide (0.76 g).

mp. 220°-230° C.

IR (Nujol): 3300, 3100, 1650, 1620, 1500 cm$^{-1}$

NMR (DMSO-d$_6$) δ: 7.07 (d, 1H, J=8 Hz), 7.36-7.67 (m, 1H), 7.80-8.10 (m, 2H), 9.13 (d, 1H, J=8 Hz), 9.26 (d, 1H, J=8 Hz), 9.80 (broad s, 1H)

(4) 3-Cyano-4H-quinolizin-4-one (4.21 g), sodium azide (1.77 g), and ammonium chloride (1.45 g) was dissolved in N,N-dimethyl-formamide (42 ml) and the resulting mixture was heated at 120° C. for two days. The reaction mixture was evaporated and the residue was dissolved in aqueous sodium bicarbonate solution and filtered. The filtrate was acidified with dilute hydrochloric acid to pH 1-2. The precipitates were filtered, washed with water and then cold N,N-dimethylformamide. The filtered solid was dissolved in hot N,N-dimethylformamide and filtered. The filtrate was treated with ether and kept at 0° C. The crystals separated were filtered and recrystallized from a mixture of ether and N,N-dimethylformamide to give 3-[5-(1H-tetrazolyl)]-4H-quinolizin-4-one (1.1 g).

mp. >250° C.

IR (Nujol): 3200, 3100, 3050, 1660, 1620, 1590 cm$^{-1}$

NMR (CF$_3$COOH) δ: 7.40 (d, 1H, J=8 Hz), 7.60-8.30 (m, 3H), 8.60 (d, 1H, J=8 Hz), 8.90 (s, 1H), 9.40-9.60 (m, 1H)

Anal. Calcd for C$_{10}$H$_7$ON$_5$: C; 56.34, H; 3.31, N; 32.85. Found: C; 56.55, H, 3.87, N; 33.02.

EXAMPLE 6

(1) A suspension of 4H-quinolizin-4-one-3-carboxylic acid (196.7 mg) in 0.1N-aqueous sodium hydroxide solution (9.9 ml) was stirred for one hour at room temperature. The resulting reaction mixture was filtered and then the filtrate was lyophilized to give sodium 4H-quinolizin-4-one-3-carboxylate (201 mg).

IR (Nujol): 1660 cm$^{-1}$

NMR (D$_2$O) δ: 6.80 (d, 1H, J=8 Hz), 7.00-7.30 (m, 1H), 7.40-7.60 (m, 2H), 8.05 (d, 1H, J=8 Hz), 8.96 (d, 1H, J=8 Hz)

(2) The following compound was obtained according to a similar manner to that of Example 6 - (1).

N-[5-(1H-Tetrazolyl)]-4H-quinolizin-4-one-3-carboxamide sodium salt.

IR (Nujol): 1670 cm$^{-1}$

NMR (D$_2$O-DMSO-d$_6$) δ: 6.80 (d, 1H, J=8Hz), 7.20-7.40 (m, 1H), 7.40-7.60 (m, 2H), 8.10 (d, 1H, J=8 Hz), 8.88 (d, 1H, J=8 Hz)

EXAMPLE 7

The following compounds were obtained according to a similar manner to that of Example 1.

(1) 4-Phenyl-1H-pyrido[1,2-a]quinolin-1-one-2-carboxylic acid.

mp: 194°-195° C.

IR (Nujol): 3150, 2650, 1740, 1725, 1590, 1440, 1115, 825 cm$^{-1}$

NMR (CF$_3$COOH, δ): 7.48-7.82 (5H, m), 7.93-8.48 (5H, m), 8.95 (1H, s), 9.70 (1H, m)

Anal. Calcd for C$_{20}$H$_{13}$NO$_3$: C; 76.18, H; 4.16, N; 4.44. Found: C; 76.32, H; 4.56, N; 4.32.

(2) 1-(1-Naphthyl)-4H-quinolizin-4-one-3-carboxylic acid.

mp: >270° C.

IR (Nujol): 1730, 1720, 1610, 770 cm$^{-1}$

NMR (CF$_3$COOH, δ): 7.10-8.37 (10H, m), 8.82 (1H, s), 9.62 (1H, m)

Anal. Calcd for C$_{20}$H$_{13}$NO$_3$.½H$_2$O: C; 74.07, H; 4.35, N; 4.32. Found: C; 74.12, H; 4.13, N; 4.22

(3) 1-(4-Biphenylyl)-4H-quinolizin-4-one-3-carboxylic acid.

mp: 261°-263° C.

IR (Nujol): 3100, 1720, 1660, 1610, 1580, 1290, 890, 775 cm$^{-1}$

NMR (CF$_3$COOH, δ): 7.20-8.47 (12H, m), 8.70 (1H, s), 9.53 (1H, m)

Anal. Calcd for C$_{22}$H$_{15}$NO$_3$.¼H$_2$O: C; 76.40, H; 4.52, N; 4.05. Found: C; 76.41, H; 4.57, N; 3.93.

(4) 1-Phenoxy-4H-quinolizin-4-one-3-carboxylic acid.

mp: 224°-226° C.

IR (Nujol): 3100, 2650, 1725, 1640, 1620, 1580, 1210, 910 cm$^{-1}$

NMR (CF$_3$COOH, δ): 7.20-7.37 (2H, m), 7.43-7.73 (3H, m), 8.78 (1H, s), 8.27 (1H, d, J=7.5 Hz), 8.60 (1H, t, J=7.5 Hz), 9.05 (1H, d, J=8.5 Hz), 9.63 (1H, d, J=7.5 Hz)

Anal. Calcd for C$_{16}$H$_{11}$NO$_4$: C; 68.33, H; 3.94, N; 4.98. Found: C; 68.45, H; 3.96, N; 4.96.

(5) 1-(3-Tolyl)-4H-quinolizin-4-one-3-carboxylic acid.

mp: 176°-178° C.

IR (Nujol): 3130, 1740, 1620, 1590, 1220, 770, 705 cm$^{-1}$

NMR (CF$_3$COOH, δ): 2.52 (3H, s), 7.17-7.67 (4H, m), 7.90-8.50 (3H, m), 8.70 (1H, s), 9.58 (1H, m)

Anal. Calcd for C$_{17}$H$_{13}$NO$_3$: C; 73.11, H; 4.69, N; 5.02. Found: C; 73.11, H; 4.85, N; 5.13.

(6) 1-(4-Chlorophenyl)-4H-quinolizin-4-one-3-carboxylic acid.

mp: 269°-271° C.

IR (Nujol): 3140, 1740, 1620, 1490, 1320, 1290, 1090, 890, 825, 775 cm$^{-1}$

NMR (CF$_3$COOH, δ): 7.35-7.78 (4H, m), 7.92-8.47 (3H, m), 8.73 (1H, s), 9.62 (1H, m)

Anal. Calcd for C$_{16}$H$_{10}$ClNO$_3$: C; 64.12, H; 3.36, N; 4.67. Found: C; 63.95, H; 3.33, N; 4.58.

(7) 1-(2-Tolyl)-4H-quinolizin-4-one-3-carboxylic acid.

mp: 168°-170° C.

IR (Nujol): 3400, 1720, 1610, 1290, 1070, 780 cm$^{-1}$

NMR (CF$_3$COOH, δ): 2.17 (3H, s), 7.25-7.75 (4H, m), 7.98-8.63 (3H, m), 8.80 (1H, s), 9.72 (1H, m)

Anal. Calcd for C$_{17}$H$_{13}$NO$_3$: C; 73.11, H; 4.69, N; 5.02. Found: C; 72.95, H; 4.91, N; 5.01.

(8) 1-(3-Methoxyphenyl)-4H-quinolizin-4-one-3-carboxylic acid.

mp: 222°-224° C.

IR (Nujol): 3100, 1725, 1600, 1490, 1220, 1030, 780 cm$^{-1}$

NMR (CF$_3$COOH, δ): 4.10 (3H, s), 7.15-8.62 (7H, m), 8.77 (1H, s), 9.62 (1H, m)

Anal. Calcd for $C_{17}H_{13}NO_4$: C; 69.15, H; 4.44, N; 4.74. Found: C; 69.67, H; 4.70, N; 4.67.

(9) 1-Hydroxy-4H-quinolizin-4-one-3-carboxylic acid.

IR (Nujol): 3200, 3100, 1690, 1620 cm$^{-1}$

NMR (CF$_3$COOH, δ): 8.00–9.50 (5H, m),

Anal. Calcd for $C_{10}N_7NO_4$: C; 58.54, H; 3.44, N; 6.83. Found: C; 57.93, H; 3.56, N; 6.77.

EXAMPLE 8

The following compounds were obtained according to a similar manner to that of Example 2.

(1) N-[5-(1H-Tetrazolyl)]-4-phenyl-1H-pyrido[1,2-a]quinolin-1-one-2-carboxamide.

mp: >270° C.

IR (Nujol): 3250, 3150, 1675, 1640, 1610, 1580, 1115 cm$^{-1}$

Anal. Calcd for $C_{21}H_{14}N_6O_2$: C; 65.96, H; 3.69, N; 21.98. Found: C; 66.43, H; 3.99, N; 22.15.

(2) N-[5-(1H-Tetrazolyl)]-(1-naphthyl)-4H-quinolizin-4-one-3-carboxamide.

mp: >270° C.

IR (Nujol): 3280, 1665, 1640, 1620, 1290, 780, 770 cm$^{-1}$

NMR (CF$_3$COOH, δ): 7.27–8.25 (10H, m), 8.77 (1H, s), 9.68 (1H, m)

Anal. Calcd for $C_{21}H_{14}N_6O_2$: C; 65.96, H; 3.69, N; 21.98.

Found: C; 60.51, H; 3.75, N; 21.91.

(3) N-[5-(1H-Tetrazolyl)]-1-(4-biphenylyl)-4H-quinolizin-4-one-3-carboxamide.

mp: >270° C.

IR (Nujol): 3180, 1670, 1625, 1590, 1100, 1035, 780, 730 cm$^{-1}$

Anal. Calcd for $C_{23}H_{16}N_6O_2$: C; 67.64, H; 3.95, N; 20.58. Found: C; 68.04, H; 4.31, N; 20.39.

(4) N-[5-(1H-Tetrazolyl)]-1-phenoxy-4H-quinolizin-4-one-3-carboxamide.

mp: >270° C.

IR (Nujol): 3200, 3150, 1660, 1620, 1590, 1010, 780, 750 cm$^{-1}$

NMR (CF$_3$COOH, δ): 7.08–7.67 (5H, m), 7.97 (1H, m), 8.22–8.47 (2H, m), 8.70 (1H, m), 9.67 (1H, m)

Anal. Calcd for $C_{17}H_{12}N_6O_3$: C; 58.62, H; 3.47, N; 24.13. Found: C; 59.39, H; 3.54, N; 24.06.

(5) N-[5-(1H-Tetrazolyl)]-1-(3-tolyl)-4H-quinolizin-4-one-3-carboxamide.

mp: >270° C.

IR (Nujol): 3160, 1670, 1640, 1620, 1600, 1585 cm$^{-1}$

NMR (CF$_3$COOH, δ): 2.52 (2H, s), 7.17–7.62 (m, 4H), 7.70–8.40 (3H, m), 8.73 (1H, s), 9.63 (1H, m)

Anal. Calcd for $C_{18}H_{14}N_6O_2$: C; 62.42, H; 4.07, N; 24.26. Found: C; 63.03, H; 4.16, N; 24.56.

(6) N-[5-(1H-Tetrazolyl)]-1-(4-chlorophenyl)-4H-quinolizin-4-one-3-carboxamide.

mp: >270° C.

IR (Nujol): 3220, 1675, 1640, 1600, 1480, 1290, 1040, 770 cm$^{-1}$

Anal. Calcd for $C_{17}H_{11}ClN_6O_2$: C; 55.67, H; 3.02, N; 22.91. Found: C; 57.45, H; 3.26, N; 21.47.

(7) N-(2-Pyridyl)-1-phenyl-4H-quinolizin-4-one-3-carboxamide.

mp: 227–229° C.

IR (Nujol): 1680, 1620, 1550, 1480, 1300, 780, 770 cm$^{-1}$

NMR (CF$_3$COOH, δ): 7.35–8.18 (10H, m), 8.35–8.77 (2H, m), 9.60 (1H, m)

Anal. Calcd for $C_{21}H_{15}N_3O_2$: C; 73.89, H; 4.43, N; 12.31. Found: C; 74.17, H; 4.61, N; 12.26.

(8) N-[5-(1H-Tetrazolyl)]-1-hydroxy-4H-quinolizin-4-one-3-carboxamide.

mp: >250° C.

IR (Nujol): 3200 (sh), 1660, 1620, 1580 cm$^{-1}$

Anal. Calcd for $C_{11}H_8N_6O_3 \cdot \frac{1}{2}H_2O$: C; 46.97, H; 3.22, N; 29.85. Found: C; 46.48, H; 3.31, N; 29.57.

(9) N-[5-(1H-Tetrazolyl)]-1-(3-methoxyphenyl)-4H-quinolizin-4-one-3-carboxamide.

mp: >270° C.

IR (Nujol): 3150, 1680, 1640, 1620, 1590, 1490, 1300, 1210, 1030, 790, 780 cm$^{-1}$ NMR (C$_3$COOH, δ): 4.13 (3H, s), 7.17–7.52 (3H, m), 7.55–8.15 (2H, m), 8.18–8.43 (2H, m), 8.80 (1H, s), 9.67 (1H, m).

Anal. Calcd for $C_{18}H_{14}N_6O_3$: C; 59.67, H; 3.89, N; 23.19. Found: C; 59.81, H; 4.19, N; 23.35.

(10) N-[5-(1H-Tetrazolyl)]-1-(2-tolyl)-4H-quinolizin-4-one-3-carboxamide.

mp: >270° C.

IR (Nujol): 3200, 3120, 1680, 1620, 1490, 1290, 1030, 780 cm$^{-1}$

NMR (CF$_3$COOH, δ): 2.15 (3H, s), 7.25–7.70 (4H, m), 7.77–8.43 (3H, m), 8.77 (1H, s), 9.77 (1H, s)

Anal. Calcd for $C_{18}H_{14}N_6O_2$: C; 62.42, H; 4.07, N; 24.26. Found: C; 62.75, H; 4.06, N; 24.35.

EXAMPLE 9

The following compounds were obtained according to a similar manner to that of Example 1.

(1) 7-(n-Butoxy)-1-phenyl-4H-quinolizin-4-one-3carboxylic acid.

mp: 155°–157° C.

IR (Nujol): 1720, 1610, 1495, 1425 cm$^{-1}$

NMR (DMSO-d$_6$, δ): 0.95 (3H, t, J=5 Hz), 1.3–2.0 (4H, m), 4.20 (2H, t, J=5 Hz), 7.3–7.7 (5H, m), 7.80 (2H, s), 8.10 (1H, s), 8.80 (1H, s), 14.1 (1H, broad s)

(2) 1-Allyloxy-4H-quinolizin-4-one-3-carboxylic acid.

mp: 140–143° C.

IR (Nujol): 3100, 1730, 1720, 1610, 1580, 1420, 1095, 1065, 770 cm$^{-1}$

NMR (CF$_3$CO$_2$H, δ): 4.90–5.13 (2H, m), 5.35–5.78 (2H, m), 5.90–6.57 (1H, m), 7.97–8.67 (3H, m), 8.77–9.03 (1H, m), 9.39–9.67 (1H, m)

(3) 1-(N-Methylanilino)-4H-quinolizin-4-one-3carboxylic acid.

mp: 185° C. (dec.)

IR (Nujol): 1720, 1700 (sh), 1620 cm$^{-1}$

NMR (CF$_3$COOH, δ): 3.58 (3H, s), 6.60–7.50 (5H, m), 7.80–8.60 (3H, m), 8.64 (1H, s), 9.50 (1H, d, J=7 Hz)

Anal. Calcd for $C_{17}H_{14}N_2O_3$: C, 69.38; H, 4.79; N, 9.52. Found: C, 69.03; H, 4.76; N, 9.31.

(4) 1-Benzyl-4H-quinolizin-4-one-3-carboxylic acid.

mp: 221°–223° C.

IR (Nujol): 3380, 1720, 1620, 1410, 1320, 1070, 1020, 780 cm$^{-1}$

Anal. Calcd for $C_{17}H_{13}NO_3$: C, 73.11; H, 4.69; N, 5.02. Found: C, 73.72; H, 4.92; N, 5.04.

(5) 1-Phenylthio-4H-quinolizin-4-one-3-carboxylic acid.

mp: 195–197° C.

IR (Nujol): 3350, 1720, 1620, 1400, 1285, 1065, 885, 780, 740 cm$^{-1}$

Anal. Calcd for $C_{16}H_{11}NO_3S'$: C, 64.63; H, 3.73; N, 4.71. Found: C, 65.04; H, 3.90; N, 4.73.

(6) 1-Phenylsulfonyl-4H-quinolizin-4-one-3-carboxylic acid.

mp: >250° C.

IR (Nujol): 1730, 1640, 1620, 1580, 1160, 1140 cm$^{-1}$

NMR (DMSO-d$_6$, δ): 7.30–8.50 (7H, m), 8.60 (1H, d, J=8 Hz), 9.00 (1H, s), 9.50 (1H, d, J=8 Hz)

Anal. Calcd for C$_{16}$H$_{11}$NO$_5$S': C, 58.35; H, 3.37. Found: C, 58.62; H, 3.31.

EXAMPLE 10

To a solution of 3-ethoxycarbonyl-1-benzoyl-4H-quinolizin-4-one (2.14 g) in chloroform (65 ml) was added dropwise trimethylsilyliodide (1.04 ml) at 0° C. After stirring for 30 minutes at 0° C., trimethylsilyliodide (1.04 ml) was added. After stirring for hour at room temperature, trimethylsilyliodide (1.04 ml) was added. After stirring for 2 hours at room temperature, the reaction mixture was diluted with chloroform and washed with water. After drying over magnesium sulfate, the chloroform extract was filtered and concentrated. The precipitate was washed with a cold chloroform to give 1-benzoyl-4H-quinolizin-4-one-3-carboxylic acid (1.252 g) as yellow crystals.

IR (Nujol): 1735, 1630, 1610, 1455, 1440, 1370 cm$^{-1}$

NMR (CDCl$_3$, δ): 6.70–8.30 (9H, m), 8.42–8.68 (1H, d, J=3 Hz)

Anal. Calcd for C$_{17}$H$_{11}$NO$_4$: C, 69.62; H, 3.78; N, 4.78. Found: C, 62.89; H, 3.54; N, 3.70.

Mass: m/e 293 (M+)

EXAMPLE 11

The following compounds were obtained according to a similar manner to that of Example 2.

(1) 7-(n-Butoxy)-1-phenyl-N-[5-(1H-tetrazolyl)]-4H-quinolizin-4-one-3-carboxamide.

mp: >205° C. (dec.)

IR (Nujol): 1670, 1635, 1580, 1370 cm$^{-1}$

NMR (DMSO-d$_6$, δ): 1.00 (3H, t, J=5.6 Hz), 1.02–2.10 (4H, m), 4.18 (2H, t, J=6 Hz), 6 80–7.25 (2H, m), 7.30–7.65 (3H, m), 7.68–8.00 (2H, m), 8.20 (1H, s), 8.87 (1H, broad s)

(2) N-[5-(1H-Tetrazolyl)]-1-phenylthio-4H-quinolizin-4-one-3-carboxamide.

mp: >270° C.

IR (Nujol): 3180, 1660, 1640, 1620, 1285, 1035, 780, 730 cm$^{-1}$

Anal. Calcd for C$_{17}$H$_{12}$N$_6$O$_2$: C, 56.04; H, 3.32; N, 23.06. Found: C, 56.61; H, 3.53; N, 23.48.

(3) 1-(N-Methylanilino)-N-[5-(1H-tetrazolyl)]-4H-quinolizin-4-one-3-carboxamide.

mp: >230° C.

IR (Nujol): 3200, 1660, 1640, 1620, 1290, 1030 cm$^{-1}$

NMR (CF$_3$COOH, δ): 3.74 (3H, s), 6.80–7.60 (5H, m), 7.62–8.08 (1H, m), 8.15–8.40 (2H, m), 8.85 (1H, s), 9.65 (1H, d, J=7 Hz)

(4) N-[5-(1H-Tetrazolyl)]-1-allyloxy-4H-quinolizin-4-one-3-carboxamide.

mp: >270° C. (dec.)

IR (Nujol): 3200, 1660, 1620, 1580, 1500, 1220, 1100, 1040, 1020, 955, 770 cm$^{-1}$ NMR (CF$_3$COOH, δ): 4.90–5.17 (2H, m), 5.37–5.80 (2H, m), 5.90–6.55 (1H, m), 8.93–9.02 (4H, m), 9.50–9.73 (1H, m)

Anal. Calcd for C$_{14}$H$_{12}$N$_6$O$_3$: C, 53.85; H, 3.87; N, 26.91. Found: C, 54.20; H, 3.81; N, 26.93.

(5) N-[5-(1H-Tetrazolyl)]-1-benzyl-4H-quinolizin-4-one-3-carboxamide.

mp: >270° C.

IR (Nujol): 3140, 1660, 1620, 1595, 1490, 1295, 1040, 1005, 775, 720, 690 cm$^{-1}$ Anal. Calcd for C$_{18}$H$_{14}$N$_6$O$_2$: C, 62.42; H, 4.07; N, 24.26. Found: C, 62.88; H, 4.54; N, 24.52.

(6) N-[5-(1H-Tetrazolyl)]-1-phenylsulfonyl-4H-quinolizin-4-one-3-carboxamide.

mp: >250° C.

IR (Nujol): 1680, 1640, 1620, 1590 cm$^{-1}$

Anal. Calcd for C$_{17}$H$_{12}$N$_6$O$_4$S: C, 51.51; H, 3.05; N, 21.20. Found: C, 51.71; H, 2.93; N, 21.83.

(7) 1-Benzoyl-N-[5-(1H-tetrazolyl)]-4H-quinolizin-4-one-3-carboxamide.

mp: >250° C.

IR (Nujol): 1690, 1630, 1380, 1240, 1120 cm$^{-1}$

NMR (CF$_3$COOH, δ): 7.40–8.25 (5H, m), 8.22–8.51 (1H, m), 8.70 (1H, broad s), 8.93 (1H, s), 9.12 (1H, d, J=9 Hz), 9.73 (1H, d, J=7 Hz)

Anal. Calcd for C$_{18}$H$_{12}$N$_6$O$_3$: C, 60 00; H, 3.36; N, 23.32. Found: C, 56.90; H, 3.80; N, 24.97.

EXAMPLE 12

The following compounds were obtained according to a similar manner to that of Example 6-(1).

(1) 1-Benzoyl-N-[5-(1H-tetrazolyl)]-4H-quinolizin-4-one-3-carboxamide sodium salt.

mp: 248°–250° C. (dec.)

IR (Nujol) 1670, 1610, 1550, 1480, 1450 cm$^{-1}$ (2) N-[5-(1H-Tetrazolyl)]-1-phenyl-4H-quinolizin-4-one-3-carboxamide sodium salt.

mp: >250° C.

IR (Nujol) 3150 (broad), 1660 (sh), 1650, 1640, 1620 cm$^{-1}$

NMR (DMSO-d$_6$, δ): 7.40–8.00 (9H, m), 8.50 (1H, s), 9.30–9.60 (1H, m)

(3) N-[5-(1H-Tetrazolyl)]-1-phenoxy-4H-quinolizin-4-one-3-carboxamide sodium salt.

mp: >250° C.

IR (Nujol): 1660 cm$^{-1}$

NMR (DMSO-d$_6$, δ): 6.9–7.8 (6H, m), 8.01 (2H, d, J=4 Hz), 8.32 (1H, s), 9.42 (1H, d, J=7 Hz), 12.30 (1H, s)

Anal. Calcd for C$_{17}$H$_{11}$N$_6$NaO$_3$: C, 55.14; H, 2.99; N, 22.70. Found: C, 54.78; H, 3.63; N, 20.44.

EXAMPLE 13

The following compound was obtained according to a similar manner to that of Example 1.

1-Benzoyl-7-n-butoxy-4H-quinolizin-4-one-3-carboxylic acid mp: 155°–156° C.

IR (Nujol): 1720, 1620, 1580, 1495 cm$^{-1}$

NMR (CDCl$_3$, δ): 1.03 (3H, t, J=6 Hz), 1.30–2.17 (4H, m), 4.23 (2H, t, J=6 Hz), 7.17–7.93 (6H, m), 8.70 (1H, s), 8.88 (1H, d, J=10 Hz), 9.02 (1H, d, J=2 Hz), 13.60 (1H, broad s)

EXAMPLE 14

The following compounds were obtained according to a similar manner to that of Example 2.

(1) 1-Benzoyl-7-n-butoxy-N-(1H-tetrazol-5-yl)-4H-quinolizin-4-one-3-carboxamide mp: 227° C.

IR (Nujol) 1680, 1660, 1625, 1585, 1550, 1495 cm$^{-1}$

NMR (DMSO-d$_6$, δ): 1.2–2.0 (4H, m), 4.23 (2H, t, J=6 Hz), 7.08 (2H, broad s), 7.37–8.17 (6H, m), 8.43 (1H, s), 8.75 (1H, d, J=10 Hz), 8.93 (1H, d, J=2 Hz)

(2) N-(4H-5-Amino-1,2,4-triazol-3-yl)-7-n-butoxy-1-phenyl-4H-quinolizin-4-one-3-carboxamide mp: 220° C.

IR (Nujol): 1690, 1650, 1490, 1465, 1450 cm$^{-1}$

NMR (DMSO-d$_6$, δ): 0.80–1.10 (3H, t), 1.30–2.10 (4H, m), 4.18 (2H, t), 7.03 (1H, s), 7.40–7.65 (5H, m), 7.70 (1H, d, J=7 Hz), 7.83 (1H, d, J=7 Hz), 8.26 (1H, s), 8.87 (1H, s)

Mass: m/e 387 (M+)

(3) 1-Ethoxycarbonyl-N-(1H-tetrazol-5-yl)-4H-quinolizin-4-one-3-carboxamide mp: >250° C.

IR (Nujol): 1665, 1640, 1610, 1595, 1580 cm$^{-1}$

Mass: m/e 328 (M+)

EXAMPLE 15

The following compounds were obtained according to a similar manner to that of Example 6-(1).

(1) 1-Benzoyl-7-n-butoxy-N-(1H-tetrazol-5-yl)-4H-quinolizin-4-one-3-carboxamide sodium salt mp: 200°–203° C.

NMR (DMSO-d$_6$, δ): 0.98 (3H, t, J=6 Hz), 1.20–2.0 (4H, m), 4.25 (2H, t, J=6 Hz), 7.32–8.17 (6H, m), 8.57 (1H, s), 8.75 (1H, d, J=10 Hz), 9.02 (1H, d, J=2 Hz), 11.87 (1H, broad s)

(2) 7-n-Butoxy-1-phenyl-N-(1H-tetrazol-5-yl)-4H-quinolizin-4-one-3-carboxamide sodium salt IR (Nujol): 1680, 1640, 1620, 1585 cm$^{-1}$ NMR (DMSO-d$_6$, δ): 0.80–1.20 (3H, m), 1.30–2.10 (4H, m), 4.00–4.48 (2H, m), 7.43–7.68 (5H, m), 7.70–7.90 (2H, m), 8.40 (1H, s), 9.00 (1H, d, J=2 Hz)

EXAMPLE 16

To a solution of 1,3-diethoxycarbonyl-4H-quinolizin-4-one (1 g) in chloroform (20 ml) was added trimethylsilyl iodide (0.49 ml) at room temperature and the mixture was stirred for 4 hours and heated with reflux for 4 hours. After cooling to room temperature, the mixture was washed with water, aqueous sodium thiosulfate, and brine. Drying over magnesium sulfate and evaporation gave a crystalline residue, which was washed with isopropyl alcohol to give 1-ethoxycarbonyl4H-quinolizin-4-one-3-carboxylic acid (794 mg).

mp: 189° C.

IR (Nujol): 1735, 1710, 1635, 1620 cm$^{-1}$

NMR (DMSO-d$_6$, δ): 1.34 (3H, t, J=7 Hz), 4.33 (2H, q, J=7 Hz), 7.45–7.95 (1H, m), 8.00–8.45 (1H, m), 8.90 (1H, s), 9.05–9.60 (2H, m),

Mass: m/e 261 (M+)

Anal. Calcd. for C$_{13}$H$_{11}$NO$_5$: C, 59.77; H, 4.24; N, 5.36. Found: C, 59.12; H, 4.59; N, 5.33.

EXAMPLE 17

To a solution of 1,3-diethoxycarbonyl-4H-quinolizin-4-one (896 mg) in methanol (9 ml) was added 6N aqueous sodium hydroxide (2.58 ml) at room temperature and the mixture was heated with reflux for an hour. After cooling to 0° C., the reaction mixture was acidified to pH 2 with 6N hydrochloric acid and the precipitate was filtered and washed with water to give 4H-quinolizin-4-one-1,3-dicarboxylic acid (202 mg).

mp: >250° C.

IR (Nujol): 1675, 1655, 1635 cm$^{-1}$

NMR (D$_2$O, NaOD, δ): 7.30–8.10, 8.65 (1H, s), 8.70–9.00 (1H, m), 9.30 (1H, d, J=7 Hz)

EXAMPLE 18

To a solution of 1-ethoxycarbonyl-N-(1H-tetrazol5-yl)-4H-quinolizin-4-one-3-carboxamide (500 mg) in N,N-dimethylformamide (5 ml) was added 1N aqueous sodium hydroxide (6 ml) at room temperature and the mixture was heated at 100° C. for an hour. After cooling to 0° C., the mixture was acidified to pH 2 with 6N hydrochloric acid and the precipitate was filtered and washed with water to give 1-carboxy-N-(1H-tetrazol-5-yl)-4H-quinolizin-4-one-3-carboxamide (280 mg).

mp: >250° C.

IR (Nujol): 1670, 1640, 1615, 1590 cm$^{-1}$

NMR (D$_2$O-NaOD, δ): 7.24–7.60 (1H, m), 7.60–8.07 (1H, m), 8.68–9.05 (1H, m), 8.84 (1H, s), 9.30 (1H, d, J=8 Hz)

Mass: m/e 272 (M+)

Anal. Calcd. for C$_{12}$H$_8$N$_6$O$_4$·H$_2$O: C, 45.29; H, 3.16; N, 26.41. Found: C, 45.29; H, 3.62; N, 26.56.

EXAMPLE 19

To a solution of pyridin-2-ylacetic acid hydrochloride (1 g) in N,N-dimethylformamide (10 ml) was added N,N'-carbonyldiimidazole (934 mg) at room temperature and the mixture was heated at 60° C. for 20 minutes. To the mixture was added 2,2-dimethyl-1,3-dioxane-4,6-dione (830 mg) at 60° C. and the mixture was stirred for 1 hour at the same temperature. The solvent was distilled off and the residue was diluted with chloroform and washed with water. The chloroform layer was extracted with aqueous sodium hydrogen carbonate and the aqueous layer was washed with chloroform and acidified to pH 2 with 6N hydrochloric acid at 0° C. and extracted with chloroform. The chloroform layer was washed with brine, dried over magnesium sulfate, and evaporated to give 2-hydroxy-4H-quinolizin-4-one-3carboxylic acid (220 mg).

mp: 194°–195° C.

IR (Nujol): 1690, 1605, 1370, 1300 cm$^{-1}$

NMR (DMSO-d$_6$, δ): 6.75 (1H, s), 7.15–7.45 (1H, m), 7.76 (2H, d), 8.90 (1H, d, J=6 Hz)

Mass: m/e 205 (M+)

Anal. Calcd. for C$_{10}$H$_7$NO$_4$: C, 58,54; H, 3.44; N, 6.83. Found: C; 58.49; H, 3.17; N, 6.86.

What we claim is:

1. A compound of the formula:

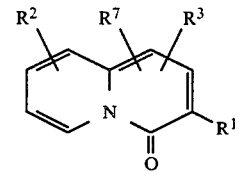

wherein $R^1$ is carboxy, carbamoyl, phenylcarbamoyl which may have hydroxy, cyano or thiocarbamoyl, $R^7$ is hydrogen or aryl selected from phenyl, tolyl, xylyl, cumenyl, naphthyl and biphenylyl;

$R^2$ is hydrogen, hydroxy, lower alkyl or lower alkoxy; and $R^3$ is hydrogen, hydroxy, lower alkyl, lower alkoxy, lower alkenyloxy, phenyl, naphthyl, biphenylyl, phenyl having one or more substituent(s) selected from halogen, lower alkyl and lower alkoxy, arylthio selected from phenylthio, tolylthio, xylylthio, cumenylthio, naphthylthio and biphenylthio, aroyl selected from benzoyl, toluoyl and naphthoyl, ar(lower)alkyl selected from phenyl(lower alkyl, tolyl(lower)alkyl, xylyl(lower)alkyl, cumenyl(lower)alkyl, naphthyl(lower)alkyl and biphenylyl(lower)alkyl, arenesulfonyl selected from benzenesulfonyl and P-toluenesulfonyl, arylamino selected from phenylamino, naphthylamino, biphenylylamino, phenylamino having lower alkyl on the nitrogen atom or aryloxy selected from phenoxy and tolyloxy;
or pharmaceutically acceptable salts thereof.

2. A compound of claim 1, wherein
$R^1$ is carboxy, carbamoyl, phenylcarbamoyl, phenylcarbamoyl having hydroxy, cyano or thiocarbamoyl,
$R^7$ is hydrogen or phenyl,
$R^2$ is hydrogen, hydroxy, lower alkyl or lower alkoxy,
$R^3$ is hydrogen, hydroxy, lower alkyl, lower alkoxy, lower alkoxycarbonyl, carboxy, lower alkenyloxy, phenyl, naphthyl, biphenyl, phenyl having a lower alkyl, phenyl having a halogen, phenyl having a lower alkoxy, phenylthio, benzoyl, phenyl(lower)alkyl, benzenesulfonyl, phenylamino having a lower alkyl on the nitrogen atom, or phenoxy.

3. A compound of claim 2, wherein
$R^1$ is carboxy, carbamoyl, phenylcarbamoyl, 2-hydroxyphenylcarbamoyl, cyano or thiocarbamoyl,
$R^2$ is hydrogen, hydroxy, methyl, ethyl or methoxy, and
$R^3$ is hydrogen, hydroxy, methyl, methoxy, isopropoxy, n-butoxy, ethoxycarbonyl, carboxy allyloxy, phenyl, naphthyl, biphenyly, 3-methylphenyl, phenoxy, 4-chlorophenyl, 2-methylphenyl, 3-methoxyphenyl, benzyl, phenylthio, benzoyl, benzenesulfonyl or N-methylanilino.

4. A compound of claim 1, wherein $R^1$ is carboxy.
5. 4H-Quinolizin-4-one-3-carboxylic acid.
6. 1-Phenyl-4H-quinolizin-4-one-3-carboxylic acid.
7. 1-Phenoxy-4H-quinolizin-4-one-3-carboxylic acid.
8. 1-Benzoyl-4H-quinolizin-4-one-3-carboxylic acid.
9. An antiulcerative composition comprising an antiulcerative effective amount of a compound of claim 1 or pharmaceutically acceptable salt thereof in association with a pharmaceutically acceptable, substantially non-toxic carrier or excipient.

10. A method for treating ulcer disease in human beings or animals which comrpises administering an antiulceratively effective amount of a compound of claim 1 or pharmaceutically acceptable salt thereof to said human beings or animals.

11. An antiallergic composition comprising an antiallergically effective amount of a compound of claim 1 or pharmaceutically acceptable salt thereof in association with a pharmaceutically acceptable, substantially non-toxic carier or excipient.

12. A method for treating allergic disease in human beings or animals which comprises administering an antiallergically effective amount of a compound of claim 1 or pharmaceutically acceptable salt thereof to said human beings or animals.

13. A compound of claim 4, wherein $R^7$ and $R^2$ are each hydrogen, and $R^3$ is lower alkyl, lower alkoxy, lower alkenyloxy, phenyl, naphthyl, biphenylyl, phenyl having one or more substituents selected from halogen, lower alkyl and lower alkoxy, arylthio selected from phenylthio, tolythio, xylylthio, cumenylthio, naphthylthio and biphenylylthio, aroyl selected from benzoyl, toluoyl and naphthoyl, ar(lower)alkyl selected from phenyl(lower)alkyl, tolyl(lower)alkyl, xylyl(lower)alkyl, cumenyl(lower)alkyl, naphthyl(lower)alkyl and biphenylyl(lower)alkyl, arenesulfonyl selected from benzenesulfonyl and p-toluenesulfonyl, arylamino selected from phenylamino, naphthylamino, biphenylylamino, phenylamino having lower alkyl on the nitrogen atom or aryloxy selected from phenyloxy and tolyloxy.

* * * * *